US005830868A

United States Patent [19]

Bolton et al.

[11] Patent Number: 5,830,868
[45] Date of Patent: Nov. 3, 1998

[54] SUBSTITUTED DI- AND TRIPEPTIDE INHIBITORS OF PROTEIN: FARNESYL TRANSFERASE

[75] Inventors: Gary Louis Bolton, Ann Arbor; Mark Wallace Creswell, Chelsea; John Cooke Hodges; Michael William Wilson, both of Ann Arbor, all of Mich.

[73] Assignee: Warner-Lambert Company, Morris Plains, N.J.

[21] Appl. No.: 671,460

[22] Filed: Jun. 27, 1996

Related U.S. Application Data

[63] Continuation of Ser. No. 303,301, Sep. 13, 1994, abandoned.
[51] Int. Cl.$^6$ ............................ A61K 38/05; A61K 38/06
[52] U.S. Cl. ................................ 514/18; 514/18; 530/331
[58] Field of Search .............................. 530/331; 514/18, 514/19

[56] References Cited

U.S. PATENT DOCUMENTS

| | | | |
|---|---|---|---|
| 4,022,759 | 5/1977 | Tinney et al. | 260/112.5 LH |

FOREIGN PATENT DOCUMENTS

| | | |
|---|---|---|
| 0457195 | 11/1991 | European Pat. Off. . |
| 0461869 | 12/1991 | European Pat. Off. . |
| 0482539 | 4/1992 | European Pat. Off. . |
| 0520823 | 12/1992 | European Pat. Off. . |
| 0523873 | 1/1993 | European Pat. Off. . |
| 0528488 | 2/1993 | European Pat. Off. . |
| 0535730 | 4/1993 | European Pat. Off. . |
| 0535731 | 4/1993 | European Pat. Off. . |
| 9116340 | 10/1991 | WIPO . |

OTHER PUBLICATIONS

T.R. Hollands, et al., *Biochemistry*, 1969, 8:2, 575–585.
K. Medzihradzeky, et al., *Biochemistry*, 1970, 9–5, 1154–1162.
*Science*, 260, 1934 (1993).
*Science*, 260, 1937 (1993).
*J. Biol. Chem.*, 268, 18415 (1993).
*Molec. Cell. Biol.*, 13, 3706 (1993).
*Cell* 57, 1167 (1989).
*Science*, 245, 379 (1989).
*Proc. Natl. Acad. Sci USA*, 86, 8323 (1989).
*Bioch. Soc. Trans.* 20, 487–88 (1992).
*J. Biol. Chem.* 268, 9675 (1993).
*Cell*, 65, 1 (1991).
*Chimica Oggi*, 10, 26 (1992).
*Microbiol. Rev.*, 53, 171 (1989).
*Hypertension*, 13, 706 (1989).
*J. Clin. Invest.* 83, 1419 (1989).
*Hypertension*, 14, 358 (1989).
*Nature Medicine*, vol. 1, 1995, Indolfi et al., pp. 541–545.
*J. Biol. Chem.*, vo. 270, No. 45, 1995, Lerner, et al., pp. 26770–26773.
*Amer. Chem. Soc.*, 1995, Vogt, et al. 6 pages.
*Nature Med.*, vol. 1, No. 8, 1995, Kohl, et al., pp. 792–797.
*Cancer Res.*, 55, 1995, Sepp–Lorenzino, et al., pp. 5302–5309.
*J. Biol.* vo. 270, 1995, Sun, et al., pp. 4243–4247.
*Proc. Natl., Acad. Sci. USA,* vo. 91, 1994, Kohl et al., pp. 9141–9145.
*Transferase Inhibitor B956,* Nagasu et al., pp. 5310–5314.
*Nature Med.* vo. 1, 1995, Lowy and Willumsen, pp. 747–748.

*Primary Examiner*—Cecilia J. Tsang
*Assistant Examiner*—Michael Borin
*Attorney, Agent, or Firm*—Todd M. Crissey

[57] ABSTRACT

Novel inhibitors of protein:farnesyl transferase enzyme are described, as well as methods for the preparation and pharmaceutical compositions of the same, which are useful in controlling tissue proliferative diseases, including cancer and restenosis.

14 Claims, No Drawings

SUBSTITUTED DI- AND TRIPEPTIDE INHIBITORS OF PROTEIN: FARNESYL TRANSFERASE

This is a continuation of U.S. Ser. No. 08/303,301, filed Sep. 13, 1994, now abandoned.

FIELD OF THE INVENTION

The present invention pertains to a number of compounds which can be used in the medicinal field to treat, prophylactically or otherwise, uncontrolled or abnormal proliferation of human tissues. More specifically, the present invention pertains to a number of compounds which act to inhibit the farnesyl transferase enzyme that has been determined to activate ras proteins which in turn activate cellular division and are implicated in cancer and restenosis.

BACKGROUND OF THE INVENTION

Ras protein (or p21) has been examined extensively because mutant forms are found in 20% of most types of human cancer and greater than 50% of colon and pancreatic carcinomas (Gibbs J. B., *Cell*, 65:1 (1991), Cartwright T., et al., *Chimica Oggi*, 10:26 (1992)). These mutant ras proteins are deficient in the capability for feedback regulation that is present in native ras and this deficiency is associated with their oncogenic action since the ability to stimulate normal cell division can not be controlled by the normal endogenous regulatory cofactors. The recent discovery that the transforming activity of mutant ras is critically dependent on post-translational modifications (Gibbs J., et al., *Microbiol. Rev.*, 53:171 (1989)) has unveiled an important aspect of ras function and identified novel prospects for cancer therapy.

In addition to cancer, there are other conditions of uncontrolled cellular proliferation that may be related to excessive expression and/or function of native ras proteins. Post surgical vascular restenosis is such a condition. The use of various surgical revascularization techniques such as saphenous vein bypass grafting, endarterectomy and transluminal coronary angioplasty is often accompanied by complications due to uncontrolled growth of neointimal tissue, known as restenosis. The biochemical causes of restenosis are poorly understood and numerous growth factors and protooncogenes have been implicated (Naftilan A. J., et al., *Hypertension*, 13:706 (1989) and *J. Clin. Invest.*, 83:1419; Gibbons G. H., et al., *Hypertension*, 14:358 (1989); Satoh T., et al., *Mollec. Cell. Biol.*, 13:3706 (1993)). The fact that ras proteins are known to be involved in cell division processes makes them a candidate for intervention in many situations where cells are dividing uncontrol- lably. In direct analogy to the inhibition of mutant ras related cancer, blockade of ras dependant processes has the potential to reduce or eliminate the inappropriate tissue proliferation associated with restenosis, particularly in those instances where normal ras expression and/or function is exaggerated by growth stimulatory factors.

Ras functioning is dependent upon the modification of the proteins in order to associate with the inner face of plasma membranes. Unlike other membrane- associated proteins, ras proteins lack conventional transmembrane or hydrophobic sequences and are initially synthesized in a cytosol soluble form. Ras protein membrane association is triggered by a series of posttranslational processing steps that are signaled by a carboxyl terminal amino acid consensus sequence that is recognized by protein:farnesyl transferase. This consensus sequence consists of a cysteine residue located four amino acids from the carboxyl terminus, followed by two lipophilic amino acids and the C-terminal residue. The sulfhydryl group of the cysteine residue is alkylated by farnesyl pyrophosphate in a reaction that is catalyzed by protein:farnesyl transferase. Following prenylation, the C-terminal three amino acids are cleaved by an endoprotease and the newly exposed alpha-carboxyl group of the prenylated cysteine is methylated by a methyl transferase. The enzymatic processing of ras proteins that begins with farnesylation enables the protein to associate with the cell membrane. Mutational analysis of oncogenic ras proteins indicate that these posttranslational modifications are essential for transforming activity. Replacement of the consensus sequence cysteine residue with other amino acids gives a ras protein that is no longer farnesylated, fails to migrate to the cell membrane and lacks the ability to stimulate cell proliferation (Hancock J. F., et al., *Cell*, 57:1617 (1989); Schafer W. R., et al., *Science*, 245:379 (1989); Casey P. J., *Proc. Natl. Acad. Sci. USA*, 86:8323 (1989)).

Recently, protein:farnesyl transferases (PFTs, also referred to as farnesyl:protein transferases) have been identified and a specific PFT from rat brain was purified to homogeneity (Reiss Y., et al., *Bioch. Soc. Trans.*, 20:487–88 (1992)). The enzyme was characterized as a heterodimer composed of one alpha-subunit (49 kDa) and one beta-subunit (46 kDa), both of which are required for catalytic activity. High level expression of mammalian PFT in a baculovirus system and purification of the recombinant enzyme in active form has also been accomplished (Chen W.-J., et al., *J. Biol. Chem.*, 268:9675 (1993)).

In light of the foregoing, the discovery that the function of oncogenic ras proteins is critically dependent on their posttranslational processing provides a means of cancer chemotherapy through inhibition of the processing enzymes. The identification and isolation of a protein:farnesyl transferase that catalyzes the addition of a farnesyl group to ras proteins provides a promising target for such intervention. Recently it has been determined that prototypical inhibitors of PFT can inhibit ras processing and reverse cancerous morphology in tumor cell models (Kohl N. E., et al., *Science*, 260:1934 (1993); James G. L., et al., *Science*, 260:1937 (1993); Garcia A. M., et al., *J. Biol. Chem.*, 268:18415 (1993)). Thus, it is possible to prevent or delay the onset of cellular proliferation in cancers that exhibit mutant ras proteins by blocking PFT. By analogous logic, inhibition of PFT would provide a potential means for controlling cellular proliferation associated with restenosis, especially in those cases wherein the expression and/or function of native ras is overstimulated.

SUMMARY OF THE INVENTION

Accordingly, the present invention is a substituted di- or tripeptide compound of Formula I:

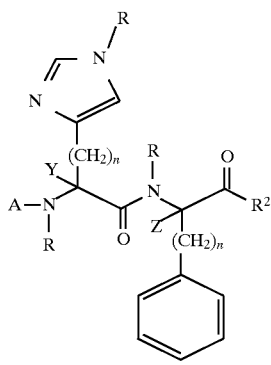

wherein:

n=1 or 2;

A=$COR^3$, $CO_2R^3$, $CONHR^3$, $CSR^3$, $C(S)OR^3$, $C(S)NHR^3$, $CF_3SO_2$, aryl-$SO_2$, or alkyl-$SO_2$, wherein $R^3$ is alkyl, $(CH_2)_m$-cycloalkyl, $(CH_2)_m$-aryl, $(CH_2)_m$-heteroaryl, or $(CH_2)_m$O-alkyl, and m=0, 1, 2, or 3;

R=independently H or Me;

Y=independently H or Me;

Z=independently H or Me;

$R^1$=H, CO-aryl, $(CH_2)_m$-aryl, $O(CH_2)_m$-cycloalkyl, $O(CH_2)_m$-aryl, or $O(CH_2)_m$-heteroaryl, wherein m is as defined above and $R^1$ is located at either the meta or para position;

X=one to four substituents, including H, alkyl, $CF_3$, F, Cl, Br, I, HO, MeO, $NO_2$, $NH_2$, $N(Me)_2$, $OPO_3H_2$, or $CH_2PO_3H_2$;

$R^2$=$NR(CH_2)_nCO_2R^3$, $NR(CH_2)_nCONHR^3$, $NR(CH_2)_nR^3$, $NR(CH_2)_{n+1}OR^4$, $NR(CH_2)_{n+1}SR^4$, $NRCH(COR^5)(CH_2)_n$-heteroaryl, $NRCH(COR^5)(CH_2)_nOR^3$, $NRCH(COR^5)(CH_2)_nSR^3$, or

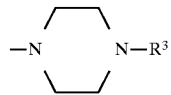

wherein R, $R^3$, and n are as defined above, $R^4$=H or $R^3$, and $R^5$=OH, $NH_2$, $OR^3$, or $NHR_3$; an optical isomer, diastereomer, or a pharmaceutically acceptable salt thereof.

The present invention is also directed to the use of a compound of Formula I, or a pharmaceutically acceptable salt therefrom, to inhibit the activity of a protein:farnesyl transferase enzyme as a method for treating tissue proliferative diseases.

A further embodiment of the present invention is the use of a pharmaceutical composition including an effective amount of a compound of Formula I as a method for the treatment of cancer.

A still further embodiment of the present invention is the use of a pharmaceutical composition including an effective amount of a compound of Formula I as a method for the treatment of restenosis.

A still further embodiment of the present invention is a pharmaceutical composition for administering an effective amount of a compound of Formula I in unit dosage form in the treatment methods mentioned above.

A final embodiment of the present invention pertains to methods for the preparation of compounds of Formula I by solid phase synthesis, solution phase synthesis, and simultaneous multiple syntheses using a multiple simultaneous synthesis apparatus.

DETAILED DESCRIPTION OF THE PREFERRED EMBODIMENTS

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "cycloalkyl" means a saturated hydrocarbon ring which contains from 3 to 10 carbon atoms, for example, cyclopropyl, cyclobutyl, cyclopentyl, cyclohexyl, adamantyl, and the like, unsubstituted or substituted by an alkyl or aryl group.

The term "aryl" means an aromatic ring which is a phenyl, 5-fluorenyl, 1-naphthyl or 2-naphthyl group, unsubstituted or substituted by 1 to 3 substituents selected from alkyl, O-alkyl and S-alkyl, O-aryl, OH, SH, F, Cl, Br, I, $CF_3$, $NO_2$, $NH_2$, $NHCH_3$, $N(CH_3)_2$, NHCO-alkyl, $(CH_2)_mCO_2H$, $(CH_2)_m$ $CO_2$-alkyl, $(CH_2)_mSO_3H$, $(CH_2)_mPO_3H_2$, $(CH_2)_mPO_3(alkyl)_2$, $(CH_2)_mSO_2NH_2$, and $(CH_2)_mSO_2NH$-alkyl wherein alkyl is defined as above and m=0, 1, 2, or 3.

The term "heteroaryl" means a heteroaromatic ring which is a 2- or 3-thienyl, 2- or 3-furanyl, 2- or 3-pyrrolyl, 2-, 3-, or 4-pyridyl, 2-, 3-, 4-, 5-, 6-, or 7-indolyl group, unsubstituted or with 1 or 2 substituents from the group of substituents described above for aryl.

The following table provides a list of abbreviations and definitions thereof used in the present invention.

| TABLE OF ABBREVIATIONS | |
|---|---|
| Abbreviation* | Amino Acid |
| Ala | Alanine |
| Arg | Arginine |
| Asn | Asparagine |
| Asp | Aspartic acid |
| Cys | Cysteine |
| Glu | Glutamic acid |
| Gln | Glutamine |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Abbreviation* | Amino Acid |
| Tyr | Tyrosine |
| Val | Valine |
| Abbreviation* | Modified and Unusual Amino Acid |
| Aaa — $CO_2R$ | An amino acid ester, for examples: Gly — $CO_2Bn$ is Glycine, benzyl ester; Ser(OBn) — $CO_2Me$ is O-Benzyl-serine, methyl ester. |
| Aaa — CONHR | An amino acid amide, for examples: Gly — CONHBn is Glycine, N-benzyl amide; Ser(OBn) — CONHEt is O-Benzyl-serine, N-ethyl amide; Tyr(OBn) — $CONHCH_2CH_2OBn$ is O-Benzyl-tyrosine, N-(2-(phenylmethoxy)ethyl) amide. |
| 3Hyp | 3-Hydroxyproline |
| 4Hyp | 4-Hydroxyproline |
| Hcy | Homocysteine |

TABLE OF ABBREVIATIONS

| | |
|---|---|
| Nva | Norvaline |
| Nle | Norleucine |
| Orn | Ornithine |
| Bal | Beta-alanine (or 3-aminopropionic acid) |
| Abu | 4-Aminobutyric acid |
| Ahe | 7-Aminoheptanoic acid |
| Acp | 6-Aminocaproic acid |
| Aoc | 8-Aminooctanoic acid |
| Apn | 5-Aminopentanoic acid |
| Bpa | (4-Benzoylphenyl)alanine |
| Chx | 3-Cyclohexylalanine (or Hexahydrophenylalanine) |
| Cit | Citrulline |

| Abbreviation* | Modified and Unusual Amino Acid |
|---|---|
| His(1-Me) | 1-Methyl-histidine (or N(τ)-Methyl-histidine) |
| His(Tr) | 1-Triphenylmethyl-histidine (or N(τ)-Trityl-histidine) |
| homoPhe | 2-Amino-4-phenylbutanoic acid (or Homophenylalanine) |
| homoTyr | 2-Amino-4-(4-hydroxyphenyl)butanoic acid (or Homotyrosine) |
| homoTyr(OBn) | 2-Amino-4-[4-(phenylmethoxy)phenyl]-butanoic acid (or O-Benzyl-homotyrosine) |
| 1-Nal | 3-(1'-Naphthyl)alanine |
| 2-Nal | 3-(2'-Naphthyl)alanine |
| Pen | Penicillamine |
| Phe(3-OBn) | (3-Benzyloxyphenyl)alanine |
| Phe(4-Ph) | 3-(1,1'Biphen-4-yl)alanine (or 4-Phenyl-phenylalanine) |
| Pgl | Phenylglycine |
| Pyr | 2-Amino-3-(3-pyridyl)-propanoic acid (or 3-Pyridylalanine) |
| Ser(OBn) | O-Benzyl-serine |
| Thr(OBn) | O-Benzyl-threonine |
| Tic | 1,2,3,4-Tetrahydro-3-isoquinoline-carboxylic acid |
| Tyr(OMe) | O-Methyl-tyrosine |
| Tyr(OEt) | O-Ethyl-tyrosine |
| Tyr(OBn) | O-Benzyl-tyrosine |
| (α-Me)Tyr(OBn) | 2-Amino-3-(4-benzyloxyphenyl)-2-methyl-propionic acid (or α-Methyl-O-benzyl-tyrosine) |
| (N—Me)Tyr(OBn) | N-Methyl-O-benzyl-tyrosine |
| Trp(For) | $N^{in}$-Formyltryptophan |

| Abbreviation | Mercapto Acids |
|---|---|
| Maa | Mercaptoacetic acid |
| Mba | 4-Mercaptobutyric acid |
| Mpa | 3-Mercaptopropionic acid |

| Abbreviation | Protecting Group |
|---|---|
| Ac | Acetyl |
| Ada | 1-Adamantyl acetic acid |
| Adoc | Adamantyloxycarbonyl |
| Bn | Benzyl |
| MeBn | 4-Methylbenzyl |
| Cbz | Benzyloxycarbonyl |
| 2-Br—Cbz | ortho-Bromobenzyloxycarbonyl |
| 2-Cl—Cbz | ortho-Chlorobenzyloxycarbonyl |
| Bom | Benzyloxymethyl |
| Boc | tertiary Butyloxycarbonyl |
| Dnp | 2,4-Dinitrophenyl |
| For | Formyl |
| Fmoc | 9-Fluorenylmethyloxycarbonyl |
| $NO_2$ | Nitro |
| TMS | Trimethylsilyl |
| Tos | 4-Toluenesulfonyl (tosyl) |
| Tr | Triphenylmethyl (trityl) |

| Abbreviation | Solvents and Reagents |
|---|---|
| HOAc | Acetic acid |
| $CF_3SO_2H$ | Trifluoromethanesulfonic acid |
| DCM | Dichloromethane |
| DCC | N,N'-Dicyclohexylcarbodiimide |
| DIC | N,N'-Diisopropylcarbodiimide |
| DIEA | N,N-Diisopropylethylamine |
| DMAP | 4-Dimethylaminopyridine |
| DMF | N,N'-Dimethylformamide |
| EDAC | N-Ethyl-N'-Dimethylaminopropyl-carbodiimide |
| EtOAc | Ethyl acetate |

| Abbreviation | Solvents and Reagents |
|---|---|
| $Et_2O$ | Diethyl ether |
| HCl | Hydrochloric acid |
| HF | Hydrofluoric acid |
| HOBT | 1-Hydroxybenzotriazole |
| KOH | Potassium hydroxide |
| MeCN | Acetonitrile |
| MeOH | Methanol |
| NHOS | N-Hydroxysuccinimide |
| NMP | N-Methylpyrrolidone |
| iPrOH | iso-Propanol |
| TBAF | Tetra n-Butylammonium Fluoride |
| TFA | Trifluoroacetic acid |

| Abbreviation | Solid Phase Peptide Synthesis Resins |
|---|---|
| HMP Resin | 4-(Hydroxymethyl)-phenoxymethyl-polystyrene resin |
| MBHA Resin | Methylbenzhydrylamine resin |
| PAM Resin | 4-(Hydroxymethyl)-phenylacetamidomethyl-polystyrene resin |
| 2-Cl—Tr Resin | 2-Chlorotrityl-polystyrene resin |
| $NH_2$-Rink Resin | 4-(amino-(2',4'-dimethoxy-phenyl)methyl)-phenoxymethyl-polystyrene resin |

| Abbreviation | Biological Reagents |
|---|---|
| FPP | Farnesyl pyrophosphate |
| PFT | Protein:farnesyl transferase |
| DTT | Dithiothreitol |
| BSA | Bovine serum albumin |

| Abbreviation | Miscellaneous |
|---|---|
| $COR^3$ | $\overset{O}{\underset{\|}{CR^3}}$ |
| $CONHR^3$ | $\overset{O}{\underset{\|}{CNHR^3}}$ |
| $CSR^3$ | $\overset{S}{\underset{\|}{CR^3}}$ |
| $C(S)OR^3$ | $\overset{S}{\underset{\|}{COR^3}}$ |
| $C(S)NHR^3$ | $\overset{S}{\underset{\|}{CNHR^3}}$ |
| $CH(COR^5)(CH_2)_nOR^3$ | $\overset{O}{\underset{\|}{(CH_2)_nCNHR^3}}$ |

-continued

TABLE OF ABBREVIATIONS

| | |
|---|---|
| CH(COR⁵)(CH₂)ₙ-heteroaryl | 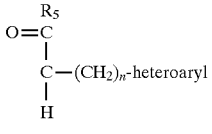 |
| CH(COR⁵)(CH₂)ₙOR³ | 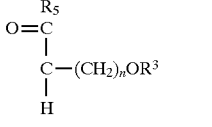 |
| CH(COR⁵)(CH₂)ₙOR³ | 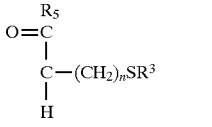 |
| CO(4-Bn-piperazin-1-yl) | 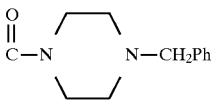 |

*If the optical activity of the amino acid is other than L(S), the amino acid or abbreviation is preceded by the appropriate configuration D(R) or DL(RS).

Preferred compounds of Formula I consist of compounds of Formula II below:

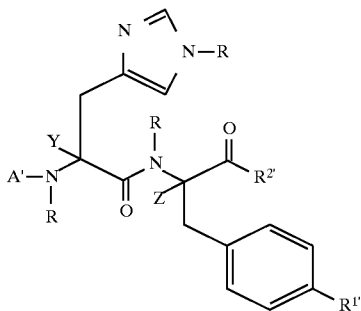

wherein:
A'=$CO_2R^3$, $CONHR^3$, $C(S)NHR^3$, or aryl-$SO_2$, wherein $R^3$ is alkyl, $(CH_2)_m$-cycloalkyl, $(CH_2)_m$-aryl, $(CH_2)_m$-heteroaryl, and m=0, 1, 2, or 3;
R=independently H or Me;
Y=independently H or Me;
z=independently H or Me;
$R^{1'}$=$(CH_2)_m$-aryl, $O(CH_2)_m$-aryl, $OPO_3H_2$, or $CH_2PO_3H_2$, wherein m is as defined above;
$R^{2'}$=$NR(CH_2)_2OR^4$, $NR(CH_2)_2SR^4$, $NRCH(COR^5)CH_2OR^3$, $NRCH(COR^5)CH_2SR^3$, or,

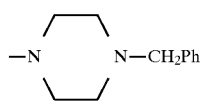

wherein R, $R^3$, and n are as defined above, $R^4$=H or $R^3$, and $R^5$=OH, $NH_2$, $OR^3$, or $NHR^3$; an optical isomer, diastereomer, or a pharmaceutically acceptable salt thereof.

Other preferred compounds of the present invention are those of Formula I as defined above wherein A is $CO_2R^3$ or $CONHR^3$; or as defined above in Formula I wherein at least one of Y and Z is Me; or as defined above in Formula I wherein $R^2$ is $(CH_2)_2OR^4$ or $CH(COR^5)CH_2OR^3$; or as defined above in Formula I wherein A is $CONHR^3$, $R^2$ is $(CH_2)_2OR^4$, and at least one of Y and Z is Me.

The most preferred compounds of Formula I include the following:
Cbz-His-Tyr(OBn)-Ser(OBn)-$CO_2$Me;
Cbz-His-Tyr(OBn)-Ser(OBn)-$CONH_2$;
Cbz-His-Tyr(OBn)-Ser(OBn)-CONHEt;
Cbz-His-Tyr(OBn)-Ser(OBn);
Cbz-His-Tyr(OBn)-D-Ser(OBn)-$CO_2$Me;
Cbz-D-His-Tyr(OBn)-Ser(OBn)-$CONH_2$;
Cbz-D-His-Tyr(OBn)-Ser(OBn)-CONHEt;
Cbz-D-His-Tyr(OBn)-Ser(OBn)-$CO_2$Me;
Cbz-D-His-Tyr(OBn)-Ser(OBn);
Cbz-His(1-Me)-Tyr(OBn)-Ser(OBn)-$CO_2$Me;
Cbz-His(1-Me)-Tyr(OBn -Ser(OBn)-$CONH_2$;
Cbz-His(1-Me)-Tyr(OBn)-Ser(OBn)-CONHEt;
Cbz-His(1-Me)-Tyr(OBn)-Ser(OBn);
Cbz-D-His(1-Me)-Tyr(OBn)-Ser(OBn)-$CO_2$Me;
Cbz-D-His(1-Me)-Tyr(OBn)-Ser(OBn)-$CONH_2$;
Cbz-D-His(1-Me)-Tyr(OBn)-Ser(OBn)-CONHEt;
Cbz-D-His(1-Me)-Tyr(OBn)-Ser(OBn);
Cbz-His-(α-Me)Tyr(OBn)-Ser(OBn)-$CO_2$Me;
Cbz-His-(α-Me)Tyr(OBn)-Ser(OBn)-$CONH_2$;
Cbz-His-(α-Me)Tyr(OBn)-Ser(OBn)-CONHEt;
Cbz-His-(α-Me)Tyr(OBn)-Ser(OBn);
Cbz-His-D-(α-Me)Tyr(OBn)-Ser(OBn)-$CO_2$Me;
Cbz-His-D-(α-Me)Tyr(OBn)-Ser(OBn)-$CONH_2$;
Cbz-His-D-(α-Me)Tyr(OBn)-Ser(OBn)-CONHEt;
Cbz-His-D-(α-Me)Tyr(OBn)-Ser(OBn);
Cbz-D-His-homoTyr(OBn)-Ser(OBn)-$CO_2$Me;
Cbz-His-Phe(4-Ph)-Ser(OBn)-$CO_2$Me;
Cbz-D-His-Phe(4-Ph)-Ser(OBn)-$CO_2$Me;
Cbz-His-Tyr(OBn)-Pyr-$CO_2$Me;
Cbz-D-His-Tyr(OBn)-Pyr-$CO_2$Me;
Cbz-His-Tyr(OBn)-$CONHCH_2CH_2OBn$;
Cbz-D-His-Tyr(OBn)-$CONHCH_2CH_2OBn$;
Cbz-His-(N-Me)Tyr(OBn)-$CONHCH_2CH_2OBn$;
Cbz-D-His-(N-Me)Tyr(OBn)-$CONHCH_2CH_2OBn$;
Cbz-His-Tyr(OBn)-$CONH(CH_2)_2Ph$;
Cbz-D-His-Tyr(OBn)-$CONH(CH_2)_2Ph$;
Cbz-His-Tyr(OBn)-Gly-$CO_2$Bn;
Cbz-D-His-Tyr(OBn)-Gly-$CO_2$Bn;
Cbz-His-Tyr(OBn)-Gly-CONHBn;
Cbz-D-His-Tyr(OBn)-Gly-CONHBn;
BnNHCO-His-Tyr(OBn)-Ser(OBn)-$CO_2$Me;
BnNHCO-His-Tyr(OBn)-Ser(OBn)-$CONH_2$;
BnNHCO-His-Tyr(OBn)-Ser(OBn)-CONHEt;
BnNHCO-His-Tyr(OBn)-Ser(OBn);
BnNHCO-His-Tyr(OBn)-$CONHCH_2CH_2OBn$;
BnNHCO-His-Tyr(OBn)-$CONHCH_2CH_2CH_2OPh$;
BnNHCO-D-His-Tyr(OBn)-Ser(OBn)-$CO_2$Me;
BnNHCO-D-His-Tyr(OBn)-Ser(OBn)-$CONH_2$;
BnNHCO-D-His-Tyr(OBn)-Ser(OBn)-CONHEt;
BnNHCO-D-His-Tyr(OBn)-Ser(OBn);
BnNHCO-D-His-Tyr(OBn)-$CONHCH_2CH_2OBn$;
BnNHCO-D-His-Tyr(OBn)-$CONHCH_2CH_2CH_2OPh$;
Cbz-His-Tyr(OBn)-$CON(Me)CH_2CH_2OBn$;
(4-EtOPh)NHCO-D-His-Tyr(OBn)-$CONH(CH_2)_3OPh$;
$PhCH_2CO$-D-His-Tyr(OBn)-$CONH(CH_2)_3$-(2-MeOPh);
(4-PhOPh)NHCO-D-His-Tyr(OBn)-$COHN(CH_2)_2Ph$; and
(4-MePh)$SO_2$-D-His-Tyr(OBn)-CO(4-Bn-piperazin-1-yl).

GENERAL METHODS FOR THE PREPARATION, EVALUATION AND USE OF COMPOUNDS OF FORMULA I

The compounds of Formula I may be prepared by solid phase peptide synthesis on a peptide synthesizer, for example, an Applied Biosystems 431A peptide synthesizer using activated esters or anhydrides of Boc or Fmoc protected amino acids, acid chlorides, isocyanates, isothiocyanates, etc., on PAM, MBHA, or $NH_2$-Rink resins with solution phase modifications to the carboxyl terminus as appropriate. Methodology for the solid phase synthesis of peptides is widely known to those skilled in the art thereof (see, for example: J. M. Stewart and J. D. Young in *Solid Phase Peptide Synthesis*; Pierce Chemical Co.; Rockford, Ill. (1984); Fields G. B. and Noble R. L., *Int. J. Peptide Protein Res.*, 35:161–214 (1990)).

Additionally, the compounds of Formula I may also be prepared by conventional solution peptide synthesis, substituting amines, acid chlorides, isocyanates, etc, for amino acid derivatives where appropriate. Methods for solution phase synthesis of peptides are widely known to those skilled in the art (see, for example, M. Bodanszky, *Principles of Peptide Synthesis, Springer-Verlag* (1984)).

Finally, the compounds of Formula I may be prepared by simultaneous multiple solid phase syntheses using an apparatus described by S. H. DeWitt, et al., *Proc. Natl. Acad. Sci. USA*, 90:6909 (1993), and referred to by the trademark, "Diversomer™" (multiple simultaneous solid phase synthesis), both trademark and apparatus being owned in whole by the Warner-Lambert Company. The multiple solid phase synthesis apparatus is currently the subject of now abandoned U.S. Ser. No. 07/958,383 filed Oct. 8, 1992 and pending continuation-in-part U.S. Ser. No. 08/012,557 filed Feb. 2, 1993.

For example (Scheme I below), Fmoc-D-His-Tyr(OBn)-$CO_2$-$CH_2CH_2Si(CH_3)_3$ is linked to 2-Cl-Tr resin using a sterically hindered amine such as DIEA as an HCl scavenger, the Fmoc protecting group is removed with piperidine, the resulting free amino terminus is acylated with a series of isocyanates, isothiocyanates, activated esters, acid chlorides and the like, the TMS-ethyl ester is cleaved with TBAF, the resulting free carboxy terminus is activated with a carbodiimide reagent such as EDAC, DCC, or DIC, the activated carboxyl group is reacted with alcohols such as HOBT, NHOS, or pentachlorophenol to give an activated ester, the activated ester is reacted with a series of amines and the resulting array of compounds of Formula I is cleaved from the resin by with hot HOAc or by treatment with TFA at room temperature.

For all three synthetic methods described above appropriate consideration is given to protection and deprotection of reactive functional groups and to the sequence of synthetic steps. Knowledge of the use of common protecting groups and strategy for the assembly of complex organic molecules are within the usual realm of expertise of a practitioner of the art of organic chemistry (see, for example: T. W. Greene and P. G. M. Wuts, *Protective Groups in Organic Chemistry*, John Wiley and Sons (1991); E. J. Corey and X.-M. Cheng, *The Logic of Chemical Synthesis*, John Wiley and Sons (1989)).

The homogeneity and composition of the resulting compounds is verified by reverse phase-high pressure liquid chromatography (RP-HPLC), capillary electrophoresis, thin layer chromatography (TLC), proton nuclear magnetic resonance spectrometry (NMR), amino acid analysis, fast atom bombardment mass spectrometry (FAB-MS) and electrospray mass spectrometry (ES-MS).

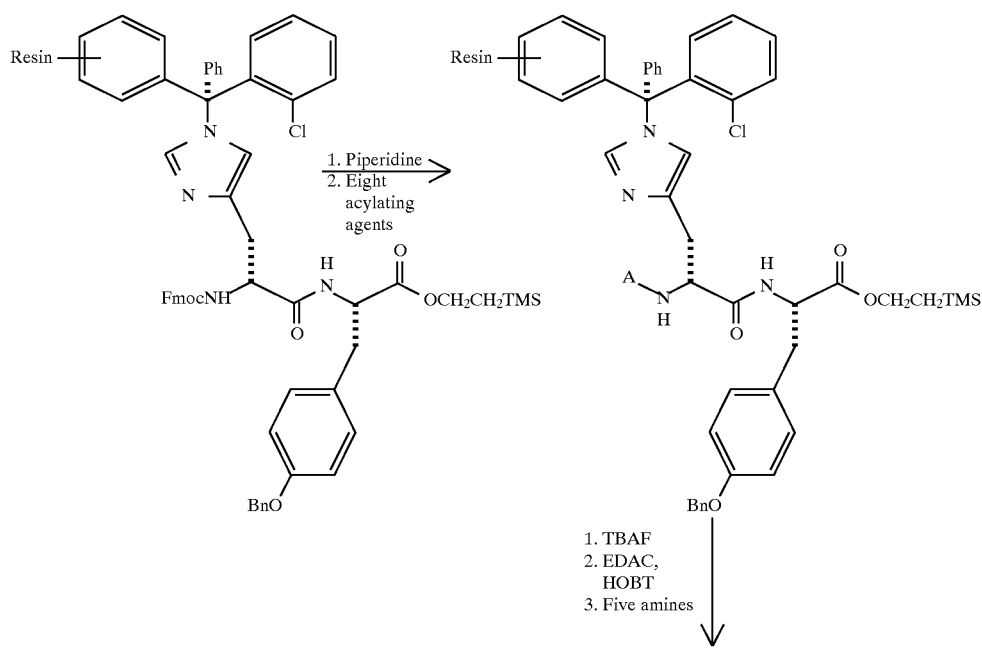

-continued
Multiple Simultaneous Synthesis Method

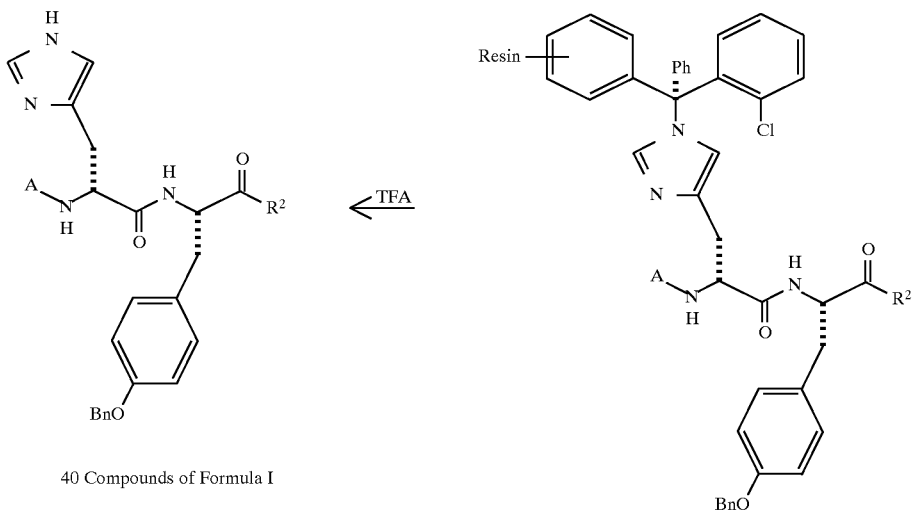

40 Compounds of Formula I

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydroiodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine (see, for example, Berge S. M., et al., "Pharmaceutical Salts," *Journal of Pharmaceutical Science,* 66:1–19 (1977)).

The acid addition salts of said basic compounds are prepared by contacting the free base form with a sufficient amount of the desired acid to produce the salt in the conventional manner. Preferably a compound of Formula I can be converted to an acidic salt by treating with an aqueous solution of the desired acid, such that the resulting pH is less than 4. The solution can be passed through a C18 cartridge to absorb the compound, washed with copious amounts of water, the compound eluted with a polar organic solvent such as, for example, methanol, acetonitrile, and the like, and isolated by concentrating under reduced pressure followed by lyophilization. The free base form may be regenerated by contacting the salt form with a base and isolating the free base in the conventional manner or as above. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts", *Journal of Pharmaceutical Science,* 66:1–19 (1977)).

The base addition salts of said acidic compounds are prepared by contacting the free acid form with a sufficient amount of the desired base to produce the salt in the conventional manner. Preferably, a compound of Formula I can be converted to a base salt by treating with an aqueous solution of the desired base, such that the resulting pH is greater than 9. The solution can be passed through a C18 cartridge to absorb the compound, washed with copious amounts of water, the compound eluted with a polar organic solvent such as, for example, methanol, acetonitrile and the like, and isolated by concentrating under reduced pressure followed by lyophilization. The free acid form may be regenerated by contacting the salt form with an acid and isolating the free acid in the conventional manner or as above. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention. Certain of the compounds of the present invention possess one or more chiral centers and each center may exist in the R(D) or S(L) configuration. The present invention includes all enantiomeric and epimeric forms as well as the appropriate mixtures thereof.

The PFT inhibitory activity of compounds of Formula I was assayed in 30 mM potassium phosphate buffer, pH 7.4, containing 7 mM DTT, 1.2 mM $MgCl_2$, 0.1 mM leupeptin, 0.1 mM pepstatin and 0.2 mM phenylmethylsulfonyl fluoride. Assays were performed in 96 well plates (Wallec) and employed solutions composed of varying concentrations of a compound of Formula I in 100% DMSO. Upon addition of both substrates, radiolabeled farnesyl pyrophosphate ([1-$^3$H], specific activity 15—30 Ci/mmol, final concentration 0.12 μM) and (biotinyl)-Ahe-Tyr-Lys-Cys-Val-Ile-Met peptide (final concentration 0.1 μM), the enzyme reaction was started by addition of 40-fold purified rat brain farnesyl protein transferase. After incubation at 37° C. for 30 minutes, the reaction was terminated by diluting the reaction 2.5-fold with a stop buffer containing 1.5M magnesium acetate, 0.2M $H_3PO_4$, 0.5% BSA, and strepavidin beads (Amersham) at a concentration of 1.3 mg/mL. After allowing the plate to settle for 30 minutes at room temperature, radioactivity was quantitated on a microBeta counter (model 1450, Wallec). Compounds of Formula I show $IC_{50}$ values of 0.5 nM to 80 μM (see data table) in this assay and are thus valuable inhibitors of protein: farnesyl transferase enzyme which may be used in the medical treatment of tissue proliferative diseases, including cancer and restenosis.

IC50 Values for Selected Compounds of Formula I Against PFT

| Example Number | IC50 (μM) |
| --- | --- |
| 1 | 4.4 |
| 4 | 1.0 |
| 5 (3) | 2.1 |
| 5 (4) | 7.3 |
| 5 (23) | 0.64 |
| 5 (27) | 30 |
| 5 (28) | 0.73 |
| 5 (30) | 73 |
| 5 (31) | 0.76 |
| 5 (35) | 66 |
| 5 (36) | 1.9 |
| 5 (46) | 1.0 |
| 5 (49) | 2.9 |
| 5 (40) | 0.75 |
| 5 (52) | 1.6 |
| 5 (56) | 1.1 |
| 5 (59) | 20 |
| 5 (60) | 1.4 |
| 5 (61) | 7.2 |
| 5 (62) | 1.5 |
| 5 (63) | 1.0 |
| 5 (64) | 1.7 |
| 5 (69) | 0.48 |
| 5 (79) | 3.0 |
| 5 (80) | 1.6 |
| 6 | 0.42 |
| 7 | 0.26 |
| 8 | 0.074 |
| 9 | 0.27 |
| 10 | 0.10 |
| 11 | 0.17 |
| 12 | 0.028 |
| 13 | 0.083 |
| 15 | 30 |
| 16 | 0.60 |
| 17 | 0.039 |
| 18 | 0.82 |
| 19 | 0.31 |
| 21 | 0.31 |
| 22 | 0.37 |
| 23 | 1.9 |
| 24 | 1.0 |
| 25 | 3.7 |
| 28 | 11 |
| 29 | 3.0 |

The compounds of the present invention can be prepared and administered in a wide variety of oral, rectal and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5 or 10 to about 70 percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsules, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as inhibitors of PFT, the compounds utilized in the pharmaceutical methods of this invention are administered at the initial dosage of about 0.01 mg/kg to about 20 mg/kg daily. A daily dose range of about 0.01 mg/kg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors' preferred methods for preparing the compounds of the invention. For added clarity, complex chemical names describing compounds of Formula I are followed by structural abbreviations, which are shown in braces, wherein the structural elements are as defined in the Table of Abbreviations above.

EXAMPLE 1

$N_\alpha$-[N-[N-[(Phenylmethoxy)carbonyl]-L-histidyl]-O-(phenylmethyl)-L-tyrosyl]-O-(phenylmethyl)-L-serinamide{Cbz-His-Tyr(OBn)-Ser(OBn)-CONH$_2$}

Using an ABI model 431A solid phase peptide synthesizer, Fmoc-NH$_2$-Rink resin (0.25 mmol scale) was treated with 20% piperidine in NMP to afford NH$_2$-Rink resin. Sequential coupling of Fmoc-protected Ser(OBn) and Tyr(OBn) (DCC and HOBT in NMP) and Fmoc deprotection (20% piperidine in NMP) reactions were run using a 4-fold excess of reagents in the coupling steps and traditional resin washing cycles to afford Tyr(OBn)-Ser(OBn)-CONH$_2$-Rink resin. This dipeptide resin was transferred to an uninstrumented reaction vessel and treated with a 4-fold excess of Cbz-His, DCC, and HOBT in DMF, shaking overnight at room temperature. After removal of excess reagents, the resulting substituted tripeptide was cleaved from the resin by treatment with 50% TFA in DCM at room temperature for 2.5 hours. Evaporation of solvents and purification by reversed phase chromatography (C$_{18}$-column, eluted with a 20–70% gradient of MeCN in water (both solvents acidified with 0.1% TFA) afforded Cbz-His-Tyr(OBn)-Ser(OBn)-CONH$_2$ as its TFA salt upon lyophilization. ES-MS: 719 (m+1).

Using analogous methods the following most preferred compounds of Formula I with carboxamides at the C-terminus may be prepared:

Cbz-D-His-Tyr(OBn)-Ser(OBn)-CONH$_2$;
Cbz-His(1-Me)-Tyr(OBn)-Ser(OBn)-CONH$_2$;
Cbz-D-His(1-Me)-Tyr(OBn)-Ser(OBn)-CONH$_2$;
Cbz-His-DL-($\alpha$-Me)Tyr(OBn)-Ser(OBn)-CONH$_2$;
BnNHCO-His-Tyr(OBn)-Ser(OBn)-CONH$_2$; and
BnNHCO-D-His-Tyr(OBn)-Ser(OBn)-CONH$_2$.

EXAMPLE 2

N-[-[N-[(Phenylmethoxy)carbonyl]-L-histidyl]-O-(phenylmethyl)-L-tyrosyl]-O-(phenylmethyl)-L-serine{Cbz-His-Tyr(OBn)-Ser(OBn)}

Beginning with PAM resin or HMP resin, Fmoc-Ser (OBn), Fmoc-Tyr(OBn), and Cbz-His are sequentially coupled using the deprotection and coupling conditions described in Example 1. Cleavage from the resin is accomplished by treatment with CF$_3$SO$_2$H for the PAM supported tripeptide or with 50% TFA in DCM for the HMP supported tripeptide. Chromatography as in Example 1 provides Cbz-His-Tyr(OBn)-Ser(OBn) as its TFA salt upon lyophilization. See also Example 7 for a solution phase method.

Using analogous methods the following most preferred compounds of Formula I with a free carboxyl terminus may be prepared:

Cbz-D-His-Tyr(OBn)-Ser(OBn);
Cbz-His(1-Me)-Tyr(OBn)-Ser(OBn);
Cbz-D-His(1-Me)-Tyr(OBn)-Ser(OBn);
Cbz-His-DL-($\alpha$-Me)Tyr(OBn)-Ser(OBn);
BnNHCO-His-Tyr(OBn)-Ser(OBn); and
BnNHCO-D-His-Tyr(OBn)-Ser(OBn).

EXAMPLE 3

Solid phase supported N-[N-[(9H-Fluoren-9-ylmethoxy)carbonyl]-L-histidyl]-O-(phenylmethyl)-L-tyrosine, 2-trimethylsilylethyl ester{Fmoc-His(2-Cl-Tr Resin)-Tyr(OBn)-CO$_2$CH$_2$CH$_2$TMS}

Step 1: Boc-Tyr(OBn)-CO$_2$CH$_2$CH$_2$TMS

2-Trimethylsilyl ethanol (2.6 g, 22.6 mmol) was added to a premixed solution of EDAC (4.3 g, 22.6 mmol), DMAP (0.5 g), and Boc-Tyr(OBn)-OH (7.0 g, 18.8 mmol) in dry THF (25 mL). The resulting mixture was stirred for 18 hours at room temperature. The solution was diluted with 1:1 EtOAc:Et$_2$O (40 mL), washed with saturated aqueous NaHCO$_3$ (2×10 mL) and with saturated aqueous NaCl (2×10 mL), dried (MgSO$_4$), filtered and concentrated in vacuo to provide an oil which was further purified by flash chromatography (SiO$_2$, EtOAc:hexane eluent) to give the pure TMS-ethyl ester as an oil;

$^1$H NMR (HCDCl$_3$): δ 0.04 (s, 9H), 1.43 (s, 9H), 3.03 (m, 2H), 4.22 (m, 2H), 4.51 (m, 1H), 4.95 (m, 1H), 5.05 (s, 2H), 6.85–7.48 (m, 9H).

Step 2: Tyr(OBn)-CO$_2$CH$_2$CH$_2$TMS

Eighty percent TFA in CH$_2$Cl$_2$ (20 mL, v/v) was added to an ice-cooled solution of Boc-Tyr(OBn)-CO$_2$CH$_2$CH$_2$TMS (14.8 g, 31.4 mmol) in CH$_2$Cl$_2$ (40 mL). The resulting mixture was stirred for 1.0 minute before concentrating in vacuo. The procedure was repeated once more, and the resulting residue was diluted with CH$_2$Cl$_2$ and saturated aqueous NaHCO$_3$. The resulting mixture was filtered through celite. The organic layer was then separated, washed with saturated aqueous NaCl, and dried (MgSO$_4$). Filtration and concentration in vacuo provided an oil which was further purified by flash chromatography (SiO$_2$, CHCl$_3$:MeOH eluent) to give the desired product;

$^1$H NMR (HCDCl$_3$): δ 0.06 (s, 9H), 1.68 (br s, 2H), 2.85–3.03 (m, 2H), 3.67 (m, 1H) , 4.22 (m, 2H) , 5.05 (s, 2H), 6.91–7.45 (m, 9H).

Step 3: Fmoc-His(Tr)-Tyr(OBn)-CO₂CH₂CH₂TMS

To a solution of HOBT (2.6 g, 19.3 mmol) in DMF (10 mL) was added Fmoc-His(Tr) ( 10.0 g, 16.1 mmol) followed by EDAC (3.7 g, 19.3 mmol). The mixture was stirred at room temperature for 20 minutes before adding a solution of Tyr(OBn)-CO₂CH₂CH₂TMS (from Step 2 above, 5.8 g, 16.1 mmol) in DMF (10 mL). The mixture was stirred overnight at room temperature before partitioning between a mixture of water and 1:1 Et₂O:EtOAc (50 ml). The layers were separated, and the organic phase was washed with saturated aqueous NaCl (4×20 mL) and dried (MgSO₄). Filtration and concentration in vacuo provided an oil which was further purified by flash chromatography (SiO₂, CHCl₃:MeOH eluent) to give the protected His-Tyr dipeptide; FAB-MS 974 (m+1).

Step 4: Fmoc-His-Tyr(OBn)-CH₂CH₂CH₂TMS

Fmoc-His(Tr)-Tyr(OBn)-CO₂CH₂CH₂TMS (from Step 3 above, 5.0 g, 5.1 mmol) was treated with pyridineoHCl (1.0 g) in MeOH (20 mL). The mixture was allowed to stir 8 hours at 65° C. The solution was concentrated in vacuo, and the residue was dissolved in CH₂Cl₂, washed with H₂O (1×), saturated aqueous NaHCO₃ (2×), and dried (MgSO₄). Filtration and concentration in vacuo provided an oil which was further purified by flash chromatography (SiO₂, CHCl₃:MeOH eluent) to give Fmoc-His-Tyr(OBn)-CO₂CH₂CH₂STMS as a white solid; FAB-MS 731 (m+1).

Step 5: Fmoc-His(2-Cl-Tr Resin)-Tyr(OBn)-CO₂CH₂CH₂TMS

To a suspension of Fmoc-His-Tyr(OBn)-CO₂CH₂CH₂TMS (from Step 4 above, 5.3 g, 7.3 mmol) in CHCl₃ (20 mL) was added 2-chloroltrityl chloride resin (Novabiochem) (7.1 g) followed by DIEA (0.96 g, 7.4 mmol). The resulting mixture was subjected to brief sonication to disperse the resin and then agitated on a shaker for 2.0 hours. The modified resin was collected by filtration, washed with DMF (2×), MeOH (2×), CHCl₂ (2×), and dried in vacuo for 18 hours to yield 10.5 g (loading corresponds to approximately 1 mmol/g resin).

EXAMPLE 4

N-[3-Phenoxypropyl]-O-(phenylmethyl)-N<sub>60</sub>-]N-[[(phenylmethyl)amino]carbonyl]-L-histidyl]-L-tyrosinamide{BnNHCO-His-Tyr(OBn)-CONH(CH₂)

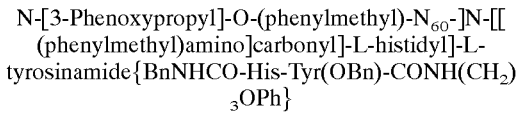

₃OPh}

Fmoc-His(2-Cl-Tr-Resin)-Tyr(OBn)-CO₂CH₂CH₂TMS (from Example 3 above, 2.0 g) was suspended in 20% piperidine in DMF. The resulting suspension was subjected to sonication for 10 minutes and then agitated by shaking for 30 minutes. The resin was filtered and washed with DMF (3×). The resin was again subjected to the same reaction conditions for an additional 20 minutes. The resin was filtered and washed with DMF (4×) and CHCl₃ (3×) to provide His(2-Cl-Tr-Resin)-Tyr(OBn)-CO₂CH₂CH₂TMS which was suspended in DCM (10 mL), agitated by shaking for 30 minutes, treated with benzyl isocyanate (1.1 g, 8.0 mmol), and agitated for an additional 30 minutes. The resin was filtered, washed with DCM (3×), resuspended in DCM, and the benzyl isocyanate treatment was repeated. The resin was filtered and washed with DMF (2×) and CHCl₃ (5×) to give BnNHCO-His(2-Cl-Tr-Resin)-Tyr(OBn)-CO₂CH₂CH₂TMS which was next suspended in a mixture of 4:3 dioxane:MeOH (14 mL) and treated with 1.0M TBAF in THF (2.0 mL, 2.0 mmol). The suspension was agitated by shaking for 18 hours, filtered, washed sequentially with a 2:1 mixture of dioxane and 10% citric acid (3×10 mL), dioxane:MeOH (3×10 mL), dioxane (3×10 mL), and CHCl₃ (3×10 mL) to provide BnNHCO-His(2-Cl-Tr-Resin)-Tyr(OBn). The BnNHCO-His(2-Cl-Tr-Resin)-Tyr(OBn) was suspended in DMF (10 mL) and treated with a carbodiimide coupling reagent such as DIC (0.2 g, 1.6 mmol) and HOBT (0.22 g, 1.6 mmol). The resulting mixture was stirred 30 minutes and 3-phenoxypropylamine (0.24 g, 1.6 mmol) was added. The resulting mixture was shaken 18 hours before filtering the resin and washing with DMF (3×) and CHCl₃ (3×). The resin was suspended in DMF (10 mL) and the carbodiimide/HOBT/3-phenoxypropylamine coupling reaction was repeated. After 18 hours, the resin was filtered and washed with 10 mL each of MeOH (2×), DCM (3×), DMF (2×), MeOH (2×), and CHCl₃ (2×) to give BnNHCO-His(2-Cl-Tr-Resin)-Tyr(OBn)-CONH(CH₂)₃OPh. The highly substiuted dipeptide was cleaved from the resin by treatment with 40% TFA in DCM, shaking for 1 hour at room temperature. The supernate, containing the free dipeptide, was filtered away from the resin and the resin was washed with DCM (6×). The combined supernate and washings were concentrated in vacuo to provide BnNHCO-His-Tyr(OBn)-CONH(CH₂)₃OPh.TFA. The product was partitioned between water and DCM, and both layers were treated dropwise with saturated aqueous NaHCO₃ until the aqueous layer remained basic. The layers were separated, and the organic phase was washed with saturated aqueous NaCl and dried (MgSO₄). Filtration and concentration yielded BnNHCO-His-Tyr(OBn)-CONH(CH₂)₃OPh; ES-MS 675 (m+1).

EXAMPLE 5

Multiple, Simultaneous Solid Phase Synthesis The method described in Example 4 may be employed in simultaneous multiple syntheses using the "Diversomer™" (Multiple simultaneous solid phase synthesis) apparatus described by S. H. DeWitt, et al., *Proc. Natl. Acad. Sci. USA*, 90:6909 (1993). Fmoc-D-His(2-Cl-Tr Resin)-Tyr(OBn)-CO₂iPr, prepared according to from Example 3 by substituting Fmoc-D-His(Tr) for Fmoc-His(Tr) in Step 3, (100–200 mg) is placed in each of 40 gas dispersion tubes, and the tubes are placed in the "Diversomer™" (Multiple simultaneous solid phase synthesis) apparatus. The sequential deprotection and coupling reactions described in Example 4 are followed, employing the following acylating agents and amines in various combinations:

| Acylating agents | Amines |
|---|---|
| 1) benzyl isocyanate | 1) 3-phenoxypropylamine |
| 2) p-toluenesulfonyl chloride | 2) 2-(phenylmethoxy)ethyl amine |
| 3) cyclohexyl isocyanate | 3) 2-[(phenylmethyl)-thio]-ethylamine |
| 4) phenyl isocyanate | 4) 4-phenylbutylamine |
| 5) i-propyl isocyanate | 5) 3-(2-methoxyphenyl)-propylamine |
| 6) n-butyl isocyanate | 6) 1-benzyl piperazine |
| 7) 4-chlorophenyl isocyanate | 7) o-benzyl-hydroxylamine |
| 8) 1-napthyl isocyanate | 8) methionine methyl ester |
| 9) 3-methoxypropyl isocyanate | 9) benzylamine |
| 10) 4-ethoxyphenyl isocyanate | 10) 2-phenylethylamine |
| 11) 2-phenethyl isocyante | |
| 12) 3-phenylpropionyl chloride | |
| 14) phenylacetyl chloride | |
| 15) 4-phenoxyphenyl isocyanate | |
| 16) benzyl chloroformate | |
| 17) (trans)-2-phenylcyclopropyl isocyanate | |
| 18) 1-adamantyl chloroformate | |

Array 1. Following cleavage from the resin and work-up as described in Example 4, the following substituted dipeptides (1–40) of Formula I are prepared:

| | |
|---|---|
| 1. PhNHCO—D—His—Tyr(OBn)—CONHCH$_2$CH$_2$OBn | |
| 2. PhNHCO—D—His—Tyr(OBn)—CONHCH$_2$CH$_2$SBn | ES-MS 677 (m + 1) |
| 3. PhNHCO—D—His—Tyr(OBn)—CONHCH$_2$CH$_2$OPh | ES-MS 661 (m + 1) |
| 4. BuNHCO—D—His—Tyr(OBn)—CONH(CH$_2$)$_4$Ph | ES-MS 639 (m + 1) |
| 5. BuNHCO—D—His—Tyr(OBn)—CO(4-Bn-piperazin-1-yl) | ES-MS 665 (m) |
| 6. (4-MePh)SO$_2$—D—His—Tyr(OBn)—CONHCH$_2$CH$_2$Ph | ES-MS 666 (m + 1) |
| 7. (4-MePh)SO$_2$—D—His—Tyr(OBn)—CONHCH$_2$CH$_2$SBn | ES-MS 712 (m + 1) |
| 8. CF$_3$SO$_2$—D—His—Tyr(OBn)—CONH—Met—CO$_2$Me | |
| 9. CF$_3$SO$_2$—D—His—Tyr(OBn)—CONHCH$_2$CH$_2$CH$_2$—(2-MeO—Ph) | |
| 10. CF$_3$SO$_2$—D—His—Tyr(OBn)—CO(4-Bn-piperazin-1-yl) | |
| 11. BnNHCO—D—His—Tyr(OBn)CONHCH$_2$CH$_2$Ph | |
| 12. MeO(CH$_2$)$_3$NHCO—D—His—Tyr(OBn)CONHOBn | |
| 13. MeO(CH$_2$)$_3$NHCO—D—His—Tyr(OBn)CONHCH$_2$CH$_2$CH$_2$OPh | |
| 14. MeO(CH$_2$)$_3$NHCO—D—His—Tyr(OBn)CONH(CH$_2$)$_3$—(2-MeO—Ph) | |
| 15. BnNHCO—D—His—Tyr(OBn)CONHCH$_2$Ph | ES-MS 631 (m + 1) |
| 16. (4-ClPh)NHCO—D—His—Tyr(OBn)CONHCH$_2$CH$_2$OBn | ES-MS 695 (m + 1) |
| 17. 1-Napthyl-NHCO—D—His—Tyr(OBn)CONHOBn | ES-MS 683 (m + 1) |
| 18. 1-Napthyl-NHCO—D—His—Tyr(OBn)CONH—Met—CO$_2$Me | ES-MS 723 (m + 1) |
| 19. (4-ClPh)NHCO—D—His—Tyr(OBn)CONH(CH$_2$)$_4$Ph | ES-MS 693 (m + 1) |
| 20. (4-ClPh)NHCO—D—His—Tyr(OBn)CONHCH$_2$Ph | ES-MS 651 (m + 1) |
| 21. BnOCO—D—His—Tyr(OBn)CONHCH$_2$CH$_2$OBn | ES-MS 676 (m + 1) |
| 22. 1-adamantyl-OCO—D—His—Tyr(OBn)CONHCH$_2$CH$_2$SBn | |
| 23. BnOCO—D—His—Tyr(OBn)CONHCH$_2$CH$_2$CH$_2$OPh | ES-MS 676 (m + 1) |
| 24. 1-adamantyl-OCO—D—His—Tyr(OBn)CONHCH$_2$CH$_2$CH$_2$CH$_2$Ph | |
| 25. BnOCO—D—His—Tyr(OBn)CO(4-Bn-piperazin-1-yl) | ES-MS 700 (m) |
| 26. PhCH$_2$CO—D—His—Tyr(OBn)CONHCH$_2$CH$_2$Ph | ES-MS 630 (m + 1) |
| 27. PhCH$_2$CH$_2$NHCO—D—His—Tyr(OBn)CONHCH$_2$CH$_2$SBn | ES-MS 705 (m + 1) |
| 28. PhCH$_2$CH$_2$NHCO—D—His—Tyr(OBn)CONH—Met—CO$_2$Me | ES-MS 701 (m + 1) |
| 29. PhCH$_2$CH$_2$NHCO—D—His—Tyr(OBn)CONH(CH$_2$)$_3$—(2-MeO—Ph) | ES-MS 703 (m + 1) |
| 30. PhCH$_2$CO—D—His—Tyr(OBn)CO(4-Bn-piperazin-1-yl) | ES-MS 684 (m) |
| 31. (t-2-Ph-c-propyl)-NHCO—D—His—Tyr(OBn)CONHCH$_2$CH$_2$Ph | ES-MS 671 (m + 1) |
| 32. (t-2-Ph-c-propyl)-NHCO—D—His—Tyr(OBn)CONHOBn | ES-MS 673 (m + 1) |
| 33. c-hexyl-NHCO—D—His—Tyr(OBn)CONH(CH$_2$)$_3$OPh | ES-MS 666 (m + 1) |
| 34. c-hexyl-NHCO—D—His—Tyr(OBn)CONH(CH$_2$)$_3$—(2-MeO—Ph) | ES-MS 681 (m + 1) |
| 35. c-hexyl-NHCO—D—His—Tyr(OBn)CONHCH$_2$Ph | ES-MS 623 (m + 1) |
| 36. PhCH$_2$CH$_2$CO—D—His—Tyr(OBn)CONHCH$_2$CH$_2$OBn | ES-MS 674 (m + 1) |
| 37. PhCH$_2$CH$_2$CO—D—His—Tyr(OBn)CONHOBn | ES-MS 646 (m + 1) |
| 38. (CH$_3$)$_2$CHNHCO—D—His—Tyr(OBn)CONH—Met—CO$_2$Me | ES-MS 639 (m + 1) |
| 39. PhCH$_2$CH—CO—D—His—Tyr(OBn)CONH(CH$_2$)$_3$Ph | ES-MS 672 (m + 1) |
| 40. (CH$_3$)$_2$CHNHCO—D—His—Tyr(OBn)CONHCH$_2$Ph | ES-MS 583 (m + 1) |

Array 2. Following cleavage from the resin and work-up as described in Example 4, the following substituted dipeptides (41–80) of Formula I are prepared:

| | |
|---|---|
| 41. n-BuNHCO—D—His—Tyr(OBn)—CONHCH$_2$CH$_2$OBn | ES-MS 641 (m + 1) |
| 42. n-BuNHCO—D—His—Tyr(OBn)—CONHCH$_2$CH$_2$SBn | ES-MS 657 (m + 1) |
| 43. n-BuNHCO—D—His—Tyr(OBn)—CONHCH$_2$CH$_2$OPh | ES-MS 641 (m + 1) |
| 44. PhNHCO—D—His—Tyr(OBn)—CONHCH$_2$CH$_2$CH$_2$Ph | ES-MS 659 (m + 1) |
| 45. PhNHCO—D—His—Tyr(OBn)—CO(4-Bn-piperazin-1-yl) | ES-MS 685 (m) |
| 46. (4-PhOPh)NHCO—D—His—Tyr(OBn)—CONHCH$_2$CH$_2$Ph | ES-MS 723 (m + 1) |
| 47. (4-PhOPh)NHCO—D—His—Tyr(OBn)—CONHCH$_2$CH$_2$SBn | ES-MS 769 (m + 1) |
| 48. (4-MePh)SO$_2$—D—His—Tyr(OBn)—CONH—Met—CO$_2$Me | ES-MS 708 (m + 1) |
| 49. (4-MePh)SO$_2$—D—His—Tyr(OBn)—CONHCH$_2$CH$_2$CH$_2$—(2-MeO—Ph) | |
| 50. (4-MePh)SO$_2$—D—His—Tyr(OBn)—CO(4-Bn-piperazin-1-yl) | ES-MS 720 (m) |
| 51. MeO(CH$_2$)$_3$NHCO—D—His—Tyr(OBn)CONHCH$_2$CH$_2$Ph | |
| 52. BnNHCO—D—His—Tyr(OBn)CONHOBn | ES-MS 647 (m + 1) |
| 53. BuNHCO—D—His—Tyr(OBn)CONHCH$_2$CH$_2$CH$_2$OPh | ES-MS 675 (m + 1) |

-continued

| | |
|---|---|
| 54. BnNHCO—D—His—Tyr(OBn)CONH(CH$_2$)$_3$—(2-MeO—Ph) | ES-MS 689 (m + 1) |
| 55. MeO(CH$_2$)$_3$NHCO—D—His—Tyr(OBn)CONHCH$_2$Ph | |
| 56. 1-napthyl-NHCO—D—His—Tyr(OBn)CONHCH$_2$CH$_2$OBn | ES-MS 711 (m + 1) |
| 57. (4-ClPh)NHCO—D—His—Tyr(OBn)CONHOBn | |
| 58. (4-ClPh)NHCO—D—His—Tyr(OBn)CONH—Met—CO$_2$Me | ES-MS 707 (m + 1) |
| 59. 1-napthyl-NHCO—D—His—Tyr(OBn)CONHCH$_2$CH$_2$CH$_2$CH$_2$Ph | ES-MS 709 (m + 1) |
| 60. 1-napthyl-NHCO—D—His—Tyr(OBn)CONHCH$_2$Ph | |
| 61. (4-EtOPh)NHCO—D—His—Tyr(OBn)CONHCH$_2$CH$_2$OBn | ES-MS 705 (m + 1) |
| 62. BnOCO—D—His—Tyr(OBn)CONHCH$_2$CH$_2$SBn | |
| 63. (4-EtOPh)NHCO—His—Tyr(OBn)CONHCH$_2$CH$_2$CH$_2$OPh | ES-MS 705 (m + 1) |
| 64. BnOCO—D—His—Tyr(OBn)CONHCH$_2$CH$_2$CH$_2$CH$_2$Ph | |
| 65. (4-EtOPh)NHCO—D—His—Tyr(OBn)CO(4-Bn-piperazin-1-yl) | ES-MS 729 (m) |
| 66. PhCH$_2$CO—D—His—Tyr(OBn)CONHCH$_2$CH$_2$Ph | ES-MS 659 (m + 1) |
| 67. PhCH$_2$CO—D—His—Tyr(OBn)CONHCH$_2$CH$_2$SBn | ES-MS 676 (m + 1) |
| 68. PhCH$_2$CO—D—His—Tyr(OBn)CONH—Met—CO$_2$Me | |
| 69. PhCH$_2$CO—D—His—Tyr(OBn)CONH(CH$_2$)$_3$—(2-MeO—Ph) | ES-MS 674 (m + 1) |
| 70. PhCH$_2$CH$_2$NHCO—D—His—Tyr(OBn)CO(4-Bn-piperazin-1-yl) | ES-MS 713 (m) |
| 71. c-hexyl-NHCO—D—His—Tyr(OBn)CONHCH$_2$CH$_2$Ph | ES-MS 637 (m + 1) |
| 72. c-hexyl-NHCO—D—His—Tyr(OBn)CONHOBn | ES-MS 639 (m + 1) |
| 73. (t-2-Ph-c-propyl)-NHCO—D—His—Tyr(OBn)CONH(CH$_2$)$_3$OPh | ES-MS 701 (m + 1) |
| 74. (t-2-Ph-c-propyl)-NHCO—D—His—Tyr(OBn)CONH(CH$_2$)$_3$—(2-MeO—Ph) | |
| 75. (t-2-Ph-c-propyl)-NHCO—D—His—Tyr(OBn)CONHCH$_2$Ph | ES-MS 657 (m + 1) |
| 76. (CH$_3$)$_2$CHNHCO—D—His—Tyr(OBn)CONHCH$_2$CH$_2$OBn | ES-MS 627 (m + 1) |
| 77. (CH$_3$)$_2$CHNHCO—D—His—Tyr(OBn)CONHOBn | ES-MS 599 (m + 1) |
| 78. PhCH$_2$CH$_2$CO—D—His—Tyr(OBn)CONH—Met—CO$_2$Me | ES-MS 686 (m + 1) |
| 79. (CH$_3$)$_2$CHNHCO—D—His—Tyr(OBn)CONHCH$_2$CH$_2$CH$_2$CH$_2$Ph | ES-MS 625 (m + 1) |
| 80. PhCH$_2$CH$_2$CO—D—His—Tyr(OBn)CONHCH$_2$Ph | ES-MS 630 (m + 1) |

EXAMPLE 6

N-[N-[N-[(Phenylmethoxy)carbonyl]-L-histidyl]-O-(phenylmethyl)-L-tyrosyl]-O-(phenylmethyl)-L-serine, methyl ester{Cbz-His-Tyr(OBn)-Ser(OBn)-CO$_2$Me}

Step 1: Boc-Tyr(OBn)-Ser(OBn)-CO$_2$Me

To a solution of Boc-Tyr(OBn) (1.88 g, 6.50 mmol) in EtOAc (30 mL) at 0° C. was added HOBT hydrate (1.19 g, 7.80 mmol) followed by DCC (1.61 g, 7.80 mmol). A solution of Ser(OBn)-CO$_2$Me.TFA (2.1 g, 6.50 mmol) in EtOAc (20 mL) was added followed by Et$_3$N (1.09 mL, 7.80 mmol). The mixture was allowed to warm to room temperature and stirred overnight. The mixture was filtered, diluted with EtOAc, and washed twice with saturated aqueous NaHCO$_3$, brine, dried over MgSO$_4$, and concentrated. Flash chromatography (40% EtOAc/hexane) gave 2.67 g (73%) of the title compound as a white solid, mp 81°–84° C.

Step 2: Tyr(OBn)-Ser(OBn)-CO$_2$Me.TFA

Boc-Tyr(OBn)-Ser(OBn)-CO$_2$Me (from Step 1 above, 2.64 g, 4.69 mmol) was dissolved in CH$_2$Cl$_2$ (15 mL), cooled to 0° C. and TFA (5 mL) was added. The solution was warmed to room temperature and stirred for 4 hours. The solution was concentrated, taken up in CH$_2$Cl$_2$ and reconcentrated twice. The resulting oil was triturated with ether to provide 2.7 g of the title compound as a white solid.

Step 3: Cbz-His-Tyr(OBn)-Ser(OBn)-CO$_2$Me

To a solution of Cbz-His (1.00 g, 3.47 mmol) in DMF (15 mL) at 0° C. was added HOBT (0.64 g, 4.16 mmol) and DCC (0.86 g, 4.16 mmol). Tyr(OBn)-Ser(OBn)-CO$_2$Me.TFA (from Step 2 above, 2.0 g, 3.47 mmol) was added followed by Et$_3$N (0.58 mL, 4.16 mmol). The mixture was allowed to warm to room temperature and stirred overnight. The mixture was filtered and the filtrate was diluted with CHCl$_3$, washed twice with saturated aqueous NaHCO$_3$, brine, dried over MgSO$_4$, and concentrated. Flash chromatography (2–5% MeOH/CHCl$_3$) gave 2.14 g of the title compound as a white solid, mp 175°–176°C.; FAB-MS 734 (m+1);

Anal. Calc. for C$_{41}$H$_{43}$N$_5$O$_8$: C, 67.11; H, 5.91; N, 9.54; Found: C, 66.96; H, 6.01; N, 9.41.

EXAMPLE 7

N-[N-[N-[(Phenylmethoxy)carbonyl]-L-histidyl]-O-(phenylmethyl)-L-tyrosyl]-O-(phenylmethyl)-L-serine{Cbz-His-Tyr(OBn)-Ser(OBn)}

To a solution of Cbz-His-Tyr(OBn)-Ser(OBn)-CO$_2$Me (from Example 6 above, 2.02 g, 2.75 mmol) in THF (50 mL) and MeOH (15 mL) at 0° C. was added 0.1N LiOH (30.3 mL, 3.03 mmol). The solution was stirred for 6 hours at 0° C., then concentrated. Water was added and the pH was adjusted to 4–5 with 1N HCl. The mixture was filtered, and the solid was collected and dried to provide 1.55 g (78%) of the title compound as a white solid, mp 187°–192°C.; ES-MS 720 (m+1);

Anal. Calc. for C$_{40}$H$_{41}$N$_5$O$_8$.1.5H$_2$O: C, 64.33; H, 5.94; N, 9.38; Found: C, 64.29; H, 5.73; N, 9.15.

EXAMPLE 8

N-[N-[N-[(Phenylmethoxy)carbonyl]-D-histidyl]-O-(phenylmethyl)-L-tyrosyl]-O-(phenylmethyl)-L-serine, methyl ester{Cbz-D-His-Tyr(OBn)-Ser(OBn)-CO$_2$Me}

Step 1: Tyr(OBn)-Ser(OBn)-CO$_2$Me.HCl

A solution of Boc-Tyr(OBn)-Ser(OBn)-CO$_2$Me (from Example 6, Step 1 above, 9.90 g, 17.6 mmol) in EtOAc was cooled to 0° C. Anhydrous HCl gas was bubbled through the cold solution for 5 minutes. The solution was allowed to warm to room temperature and stirred overnight. The solution was concentrated, taken up in EtOAc and reconcentrated to provide 8.75 g of the title compound as a foam; CI-MS 463 (m+1).

Step 2: Cbz-D-His(Tr)-Tyr(OBn)-Ser(OBn)-CO$_2$Me

According to Example 6, Step 3, by substituting Cbz-D-His(Tr) for Cbz-His and Tyr(OBn)-Ser(OBn)-CO$_2$Me.HCl for Tyr(OBn)-Ser(OBn)-CO$_2$Me.TFA, the title compound was obtained as a white solid, mp 78°–88°C.; FAB-MS 976 (m+1).

Step 3: Cbz-D-His-Tyr(OBn)-Ser(OBn)-CO$_2$Me

A solution of Cbz-D-His(Tr)-Tyr(OBn)-Ser(OBn)-CO$_2$Me (from Step 2 above, 0.27 g, 0.28 mmol) in HOAc:H$_2$O (4:1, 2 mL) was stirred at 80° C. for 5 minutes, then cooled to room temperature. The solution was partitioned between EtOAc and saturated aqueous NaHCO$_3$. The organic layer was washed with brine, dried (MgSO$_4$), and concentrated. Flash chromatography (2–5% MeOH:CHCl$_3$) yielded 0.10 g of the title compound as a foam; FAB-MS 734 (m+1).

EXAMPLE 9

N-[N-[N-[(Phenylmethoxy)carbonyl]-L-histidyl]-O-(phenylmethyl)-L-tyrosyl]-O-(phenylmethyl)-D-serine, methyl ester{Cbz-His-Tyr(OBn)-D-Ser(OBn)-CO$_2$Me}

According to Example 6, by substituting D-Ser(OBn)-CO$_2$Me.TFA for Ser(OBn)-CO$_2$Me.TFA in Step 1, the title compound was obtained, mp 168°–170°C.; FAB-MS 734 (m+1). EXAMPLE 10

N-[α-Methyl-N-[N-[(phenylmethoxy)carbonyl]-L-histidyl]-O-(phenylmethyl)-DL-tyrosyl]-O-(phenylmethyl)-L-serine. methyl ester{Cbz-His-DL-(α-Me)Tyr(OBn)-Ser(OBn)-CO$_2$Me}

According to Example 6, by substituting Boc-DL-(α-Me)Tyr(OBn) for Boc-Tyr(OBn) in Step 1, the title compound was obtained; FAB-MS 748 (m+1).

EXAMPLE 11

N-Ethyl-N$_\alpha$-[N-[N-[(phenylmethoxy)carbonyl]-L-histidyl]-O-(phenylmethyl)-L-tyrosyl]-O-(phenylmethyl)-L-serinamide{Cbz-His-Tyr(OBn)-Ser(OBn)-CONHEt}

According to Example 6, by substituting Boc-Tyr(OBn)-Ser(OBn)-CONHEt for Boc-Tyr(OBn)-Ser(OBn)-CO$_2$Me in Step 2, the title compound was obtained, mp 182°–188°C.; FAB-MS 747 (m+1).

EXAMPLE 12

N-Ethyl-N$_\alpha$-[N-[N-[(Phenylmethoxy)carbonyl]-D-histidyl]-O-(phenylmethyl)-L-tyrosyl]-O-(phenylmethyl)-L-serinamide{Cbz-D-His-Tyr(OBn)-Ser(OBn)-CONHEt}

According to Example 6, by substituting Boc-Tyr(OBn)-Ser(OBn)-CONHEt for Boc-Tyr(OBn)-Ser(OBn)-CO$_2$Me in Step 2 and Cbz-D-His for Cbz-His in Step 3, the title compound was obtained, mp 193°–196° C.; ES-MS 747 (m+1).

EXAMPLE 13

N-[N-[1-Methyl-N-[(phenylmethoxy)carbonyl]]-L-histidyl]-O-(phenylmethyl)-L-tyrosyl]-O-(phenylmethyl)-L-serine. methyl ester{Cbz-His(1-Me)-Tyr(OBn)-Ser(OBn)-CO$_2$Me Step 1: Cbz-His(1-Me)

Benzyl chloroformate (0.24 mL, 1.7 mmol) was added dropwise to a slurry of 1-methyl-L-histidine (0.25 g, 1.5 mmol) in THF (5 mL) and saturated aqueous NaHCO$_3$, (5 mL) at 0° C. The mixture was allowed to warm to room temperature and stirred overnight. The mixture was concentrated and diluted with H$_2$O, washed with ether, and the pH adjusted to 6–7 with iN HCl. The mixture was concentrated, then diluted with CHCl$_3$ (150 mL) and MeOH (15 mL), and stirred for 1 hour. The mixture was dried (MgSO$_4$) and concentrated to provide 0.48 g of the title compound which was used without further purification.

Step 2: Cbz-His(1-Me)-Tyr(OBn)-Ser(OBn)-CO$_2$Me

To a slurry of Cbz-His(1-Me) (from Step 1 above, 0.36 g, 1.2 mmol), Tyr(OBn)-Ser(OBn)-CO$_2$Me.HCl (from Example 8, Step 1 above, 0.60 g, 1.2 mmol), DCC (0.30 g, 1.4 mmol), and HOBT (0.19 g, 1.4 mmol) in CH$_2$Cl$_2$ was added Et$_3$N (0.17 mL, 1.2 mmol) and the mixture was stirred overnight at room temperature. The mixture was diluted with CHCl$_3$, washed with saturated aqueous NaHCO$_3$, brine, dried (MgSO$_4$), and concentrated. Flash chromatography (1% MeOH:CHCl$_3$) provided the title compound as a white solid, mp 161.5°–163.5° C.; FAB-MS 748 (m+1).

EXAMPLE 14

N-[N-[1-Methyl-N-[(phenylmethoxy)carbonyl]-D-histidyl]-O-(phenylmethyl)-L-tyrosyl]-O-(phenylmethyl)-L-serine. methyl ester{Cbz-D-His(1-Me)-Tyr(OBn)-Ser(OBn)-CO$_2$Me}

According to Example 13, by substituting 1-methyl-D-histidine for 1-methyl-L-histidine, the title compound was obtained; FAB-MS 748 (m+1).

EXAMPLE 15

N-[L-2-Amino-N-[N-[(Phenylmethoxy)carbonyl]-D-histidyl]-4-[4-(phenylmethoxy)phenyl]butanoyl]-O-(phenylmethyl-L-serine, methyl ester{Cbz-D-His-homoTyr(OBn)-Ser(OBn)-CO$_2$Me}

According to Example 6, by substituting Boc-homoTyr (OBn) for Boc-Tyr(OBn) in Step 1, and substituting Cbz-D-His for Cbz-His in Step 3, the title compound was obtained; ES-MS 748 (m+1).

EXAMPLE 16

N-[4-Phenyl-N-[N-[(phenylmethoxy)carbonyl]-L-histidyl]-L-phenylalanyl]-O-(phenylmethyl)-L-serine, methyl ester{Cbz-His-Phe(4-Ph)-Ser(OBn)-CO$_2$Me}

According to Example 6, by substituting Boc-Phe(4-Ph) for Boc-Tyr(OBn) in Step 1, the title compound was obtained, mp 184°–187°C.; FAB-MS 704 (m+1).

EXAMPLE 17

N-[O-(Phenylmethyl)-N[N-[[(Phenylmethyl)amino]-carbonyl]-L-histidyl]-L-tyrosyl]-O-(phenylmethyl)-serine, methyl ester{BnNHCO-His-Tyr(OBn)-Ser(OBn)-CO$_2$Me}

Step 1: Fmoc-His(Tr)-Tyr(OBn)-Ser(OBn)-CO$_2$Me

According to Example 13, Step 2, by substituting Fmoc-His(Tr) for Cbz-His(1-Me), the title compound was obtained, mp 82°–92° C.

Step 2: His(Tr)-Tyr(OBn)-Ser(OBn)-CO$_2$Me

Piperidine (4.0 mL) was added to a slurry of Fmoc-His(Tr)-Tyr(OBn)-Ser(OBn)-CO$_2$Me (from Step 1 above, 1.85 g, 1.74 mmol) in CH$_2$Cl$_2$ (20 mL). The solution was stirred for 2 hours at room temperature, then concentrated. The residue was taken up in EtOAc (150 mL), washed with water (3×50 mL), dried (MgSO$_4$), and concentrated. The resulting oil was triturated with Et$_2$O/hexane. Flash chromatography of the residue (2% MeOH/CHCl$_3$) gave 1.03 g of the title compound as a foam, mp 61.5°–70°C.; ES-MS 843 (m+1).

Step 3: BnNHCO-His(Tr)-Tyr(OBn)-Ser(OBn)-CO$_2$Me

Benzyl isocyanate (0.053 mL, 0.43 mmol) was added in one portion to a solution of His(Tr)-Tyr(OBn)-Ser(OBn)-CO$_2$Me (from Step 2 above, 0.33 g, 0.39 mmol) in EtOAc (5 mL). The resulting slurry was stirred for 3 hours at room temperature, then concentrated to yield the title compound (0.4 g), which was used without further purification.

Step 4: BnNHCO-His-Tyr(OBn)-Ser(OBn)-CO$_2$Me

According to Example 8, by substituting BnNHCO-His(Tr)-Tyr(OBn)-Ser(OBn)-CO$_2$Me for Cbz-His(Tr)-Tyr(OBn)-Ser(OBn)-CO$_2$Me, the title compound was obtained, mp 196.5°–199°C.; ES-MS 733 (m+1).

EXAMPLE 18

N-[N-[N-(1-Oxo-3-phenylpropyl)-L-histidyl]-O-(phenylmethyl)-L-tyrosyl]-O-(phenylmethyl)-L-serine. methyl ester{PhCH$_2$CH$_2$CO-His-Tyr(OBn)-Ser(OBn)-CO$_2$Me}

Step 1: PhCH$_2$CH$_2$CO-His(Tr)-Tyr(OBn)-Ser(OBn)-CO$_2$Me

To a cooled (0° C.) solution of His(Tr)-Tyr(OBn)-Ser(OBn)-CO$_2$Me (from Example 17, Step 2 above, 0.33 g, 0.39 mmol) in THF (5 mL) was added Et$_3$N (0.06 mL, 0.43 mmol) followed by phenylpropionyl chloride (0.064 mL, 0.43 mmol). The resulting slurry was brought to room temperature and stirred overnight. The mixture was partitioned between EtOAc and saturated aqueous NaHCO$_3$. The organic layer was washed with brine, dried (MgSO$_4$), and concentrated to yield the title compound as a solid which was used without further purification.

Step 2: PhCH$_2$CH$_2$CO-His-Tyr(OBn)-Ser(OBn)-CO$_2$Me

According to Example 8, Step 3, by substituting PhCH$_2$CH$_2$CO-His(Tr)-Tyr(OBn)-Ser(OBn)-CO$_2$Me for Cbz-D-His(Tr)-Tyr(OBn)-Ser(OBn)-CO$_2$Me, the title compound was obtained, mp 193°–196.5° C.; ES-MS 732 (m+1).

EXAMPLE 19

N$_\alpha$-[-N-[(Phenylmethoxy)carbonyl]-L-histidyl]-O-(phenylmethyl)-N-[2-(phenylmethoxy)ethyl]-L-tyrosinamide{Cbz-His-Tyr(OBn)-CONHCH$_2$CH$_2$OBn}

Step 1: Cbz-His-Tyr(OBn)-CO$_2$Me

According to Example 6, Step 3, by substituting Tyr(OBn)-CO$_2$Me.TFA for Tyr(OBn)-Ser(OBn)-CO$_2$Me.TFA, the title compound was obtained as a white powder, mp 145°–148°C.; CI-MS 557 (m+1).

Step 2: Cbz-His-Tyr(OBn)

According to Example 7, by substituting Cbz-His-Tyr(OBn)-CO$_2$Me for Cbz-His-Tyr(OBn)-Ser(OBn)-CO$_2$Me, the title compound was obtained as a white powder, mp 79°–92°C.; CI-MS 543 (m+1).

Step 3: Cbz-His -Tyr(OBn)-CONHCH$_2$CH$_2$OBn

To a solution of Cbz-His-Tyr(OBn) (from Step 2 above, 0.43 g, 0.79 mmol) in DMF (4 mL) at 0° C. was added HOBT (0.15 g, 0.95 mmol) and DCC (0.20 g, 0.95 mmol). A solution of 2-(phenylmethoxy)ethylamine (0.12 g, 0.79 mmol) in DMF (1 mL) was then added. The mixture was allowed to warm to room temperature and stirred overnight. The mixture was filtered, diluted with CHCl$_3$, washed twice with saturated aqueous NaHCO$_3$, washed with brine, dried over MgSO$_4$, and concentrated. Flash chromatography (3–5% MeOH/CHCl$_3$) afforded 0.34 g (63%) of the title compound as a white solid, mp 136°–150° C.; FAB-MS 676 (m+1);

Anal. Calc. for C$_{39}$H$_{41}$N$_5$O$_6$: C, 69.32; H, 6.12; N, 10.36; Found: C, 69.43; H, 6.24; N, 10.45.

EXAMPLE 20

N$_\alpha$-[N-[(Phenylmethoxy)carbonyl]-D-histidyl]-N-[2-(phenylmethoxy)ethyl]-O-(phenylmethyl)-L-tyrosinamide{Cbz-D-His-Tyr(OBn)-CONHCH$_2$CH$_2$OBn}

According to Example 6, by substituting 2-(phenylmethoxy)ethylamine for Ser(OBn)-TFA and omitting Et$_3$N in Step 1 and by substituting Cbz-D-His for Cbz-His in Step 3, the title compound was prepared, mp 161°–165°C.; FAB-MS 676 (m+1).

EXAMPLE 21

N$_\alpha$-[N-Methyl-N[(phenylmethoxy)carbonyl]-D-histidyl]-N-[2-(phenylmethoxy)ethyl]-O-(phenylmethyl)-L-tyrosinamide{Cbz-D-His-(N-Me)Tyr(OBn)-CONHCH$_2$CH$_2$OBn}

According to Example 20, by substituting Boc-(N-Me)Tyr(OBn) for Boc-Tyr(OBn), the title compound was obtained, mp 64°–78°C.; ES-MS 690 (m+1).

EXAMPLE 22

N$_\alpha$-[α-Methyl-N-[N-[(phenylmethoxy)carbonyl]-D-histidyl]-N-[2-(phenylmethoxy)ethyl]-O-(phenylmethyl)-L-tyrosinamide{Cbz-D-His-(α-Me)Tyr(OBn) -CONHCH$_2$CH$_2$OBn}

According to Example 20, by substituting Boc-(α-Me)Tyr(OBn) for Boc-Tyr(OBn), the title compound was obtained, mp 66°–78°C.; ES-MS 690 (m+1).

EXAMPLE 23

N-(2-Phenylethyl)-N$_{60}$ -[-N-[(phenylmethoxy)carbonyl]-L-histidyl]-O-(phenylmethyl)-L-tyrosinamide{Cbz-His-Tyr(OBn)-CONHCH$_2$CH$_2$Ph}

According to Example 19, Step 3, by substituting 2-phenylethylamine for 2-(phenylmethoxy) ethylamine, the title compound was obtained as a white solid, mp 188°–189.5° C.; FAB-MS 646 (m+1).

EXAMPLE 24

N-[N-[N-[(Phenylmethoxy)carbonyl]-L-histidyl]-O-(phenylmethyl)-L-tyrosyl]-3-(3-pyridinyl)-L-alanine, methyl ester{Cbz-His-Tyr(OBn)-Pyr-CO$_2$Me}

According to Example 19, Step 3, by substituting Pyr-CO$_2$Me for 2-(phenylmethoxy)ethylamine, the title compound was obtained as a white solid, mp 180°–182.5° C. (dec); FAB-MS 705 (m+1).

EXAMPLE 25

(S,R)-N-[2-(4-Benzyloxy-phenyl)-1-(3-phenoxy-propylcarbamoyl)-ethyl]-2-[3-(4-ethoxy-phenyl)-ureido]-3-(3H-imidazol-4-yl)-propionamide{(4-EtOPh)NHCO-D-His-Tyr(OBn)-CONH(CH$_2$)$_3$OPh}

Step 1. Boc-Tyr(OBn)-CONH(CH$_2$)$_3$OPh 2-(Phenylmethoxy)ethylamine (0.81 g, 5.4 mmol) was added to a premixed solution of EDAC (1.2 g, 6.5 mmol), HOBT (0.87 g, 6.5 mmol), and Boc-Tyr(OBn)-OH (2.0 g, 5.4 mmol) in dry DMF (15 mL). The resulting mixture was stirred for 18 hours at room temperature. The solution was diluted with 1:1 EtOAc:Et$_2$O (40 mL), washed with saturated aqueous NaCl (4×10 mL), dried (MgSO$_4$), filtered, and concentrated in vacuo to provide a solid which was further purified by trituration with hexane to give the pure product, mp 145°–146° C.

Step 2. Tyr(OBn)-CONH(CH$_2$)$_3$OPh

Dry HCl gas was bubbled into an ice cold solution of Boc-Tyr(OBn)-CONH(CH$_2$)$_3$OPh (from Step 1 above, 2.0 g, 3.9 mmol) in MeOH (15 mL) for 4 minutes. The resulting mixture was stirred for 1 hour at 0° C. and then allowed to warm to room temperature and stir 1 hour. The solution was concentrated in vacuo to provide a solid which was triturated with ether to provide Tyr(OBn)-CONH(CH$_2$)$_3$OPh.HCl; CI-MS 405 (m+1). The title compound was suspended in CHCl$_3$, cooled in an ice bath, and NH$_4$Cl gas was bubbled through the mixture for 2 minutes. The NH$_4$Cl was filtered off, and the supernate was concentrated in vacuo to yield the free base of the title compound which was used in the next step without further purification.

Step 3. Fmoc-D-His(Tr)-Tyr(OBn)-CONH(CH$_2$)$_3$OPh

To a solution of HOBT (0.48 g, 3.5 mmol) in DMF (10 mL) was added Fmoc-D-His(Tr)-CO$_2$H (2.0 g, 3.2 mmol) followed by EDAC (0.67 g, 3.5 mmol). The mixture was stirred at room temperature for 20 minutes before adding a solution of Tyr(OBn)-CONH(CH$_2$)$_3$OPh (from Step 2 above, 1.4 g, 3.2 mmol) in DMF (10 mL). The mixture was stirred overnight at room temperature before partitioning between a mixture of water (20 mL) and 1:1 Et$_2$O:EtOAc (50 mL). The layers were separated, and the organic phase was washed with saturated aqueous NaCl (4×20 mL) and dried (MgSO$_4$). Filtration and concentration in vacuo provided an oil which was further purified by flash chromatography (SiO$_2$, CHCl$_3$: MeOH eluent) to give the protected His-Tyr dipeptide; FAB-MS 1006 (m).

Step 4. D-His(Tr)-Tyr(OBn)-CONH(CH$_2$)$_3$OPh

Fmoc-D-His(Tr)-Tyr(OBn)-CONH(CH$_2$)$_3$OPh (from Step 3 above, 1.0 g, 0.99 mmol) in CH$_2$Cl$_2$ (5 mL) was treated with piperidine (0.18 g, 2.1 mmol). The resulting mixture was stirred 2 hours before concentrating in vacuo and purifying the resulting oil by flash chromatography (SiO$_2$CHCl$_{13}$:MeOH eluent) to give (4-EtOPh)NHCO-D-His(Tr)-Tyr(OBn)-CONH(CH$_2$)$_3$OPh; ES-MS 784 (m+1).

Step 5. (4-EtOPh)NHCO-D-His(Tr)-Tyr(OBn)-CONH(CH$_2$)$_3$OPh

D-His(Tr)-Tyr(OBn)-CONH(CH$_2$)$_3$OPh (from Step 4 above, 0.55 g, 0.7 mmol) in CH$_2$Cl$_2$ (5 mL) was treated with 4-ethoxyphenyl isocyanate (0.1 g, 0.7 mmol). The mixture was stirred 1 hour at room temperature. Concentrated in vacuo. The resulting oil was purified by flash chromatography (SiO$_2$, CHCl$_3$:MeOH eluent) to give (4-EtOPh)NHCO-D-His(Tr)-Tyr(OBn)-CONH(CH$_2$)$_3$OPh; ES-MS 947 (m+1).

Step 6. (4-EtOPh)NHCO-D-His-Tyr(OBn)-CONH(CH$_2$)$_3$OPh (4-EtOPh)NHCO-D-His(Tr)-Tyr(OBn)-CONH(CH$_2$)$_3$OPh (from Step 5 above, 0.5 g, 0.52 mmol) in MeOH (5 mL) was treated with Pyridine HCl (catalytic). The resulting mixture was stirred at 65° C. for 6 hours. Concentrated in vacuo to obtain an oil which was purified by by flash chromatography (SiO$_2$, CHCl$_3$:MeOH eluent) to give (4-EtO-Ph)NHCO-D-His-Tyr(OBn)-CONH(CH$_2$)$_3$OPh, mp 185°–187° C.; ES-MS 705 (m+1).

EXAMPLE 26

(S,R)-N-{2-(4-Benzyloxy-phenyl)-1-(3-(2-methoxy-phenyl)-propylcarbamoyl]-ethyl}-3-(3H-imidazol-4-yl)-2-phenylacetylamino-propionamide{PhCH$_2$CO-D-His- Tyr(OBn)-CONH(CH$_2$)$_3$(2-MeOPh)}

Step 1. Boc-Tyr(OBn)-CONH(CH$_2$)$_3$(2-MeOPh)

According to Example 25, Step 1, by substituting 3-(2-methoxyphenyl) propyl amine for 2-(phenylmethoxy)-ethylamine, the title compound was obtained as a white solid, mp 125°–126.5° C.

Step 2. Tyr(OBn)-CONH(CH$_2$)$_3$(2-MeOPh)

According to Example 25, Step 2, by substituting Boc-Tyr(OBn)-CONH(CH$_2$)$_3$(2-MeOPh) for Boc-Tyr(OBn)-CONH(CH$_2$)$_3$OPh, the title compound was obtained as a white solid; CI-MS 419 (m+1).

Step 3. Fmoc-D-His(Tr)-Tyr(OBn)-CONH(CH$_2$)$_3$(2-MeOPh)

According to Example 25, Step 3, by substituting Tyr(OBn)-CONH(CH$_2$)$_3$(2-MeOPh) for Tyr(OBn)-CONH(CH$_2$)$_3$OPh, the title compound was obtained as a foam; ES-MS 1020 (m).

Step 4. D-His(Tr)-Tyr(OBn)-CONH(CH$_2$)$_3$(2-MeOPh)

According to Example 25, Step 4, by substituting Fmoc-D-His(Tr)-Tyr(OBn)-CONH(CH$_2$)$_3$(2-MeOPh) for Fmoc-D-His(Tr)-Tyr(OBn)-CONH(CH$_2$)$_3$OPh, the title compound was obtained as a white foam; ES-MS 798 (m+1).

Step 5. PhCH$_2$CO-D-His(Tr)-Tyr(OBn)-CONH(CH$_2$)$_3$(2-MeOPh)

To a solution of D-His(Tr)-Tyr(OBn)-CONH(CH$_2$)$_3$(2-MeOPh) (0.4 g, 0.5 mmol) in CH$_2$Cl$_2$ (5 mL) was added N-methyl morpholine (0.05 g, 0.5 mmol) followed by phenyl acetyl chloride (0.08 g, 0.5 mmol). The resulting mixture was stirred 2 hours at room temperature. Diluted with DCM and washed with saturated aqueous NaHCO$_3$, saturated aqueous NaCl, and dried (MgSO$_4$). Purified by flash chromatography (SiO$_2$, CHCl$_3$:MeOH eluent). The title compound was obtained as a foam; FAB-MS 916 (m).

Step 6. PhCH$_2$CO-D-His(Tr)-Tyr(OBn)-CONH(CH$_2$)$_3$(2-MeOPh)

According to Example 25, Step 6, by substituting PhCH$_2$CO-D-His(Tr)-Tyr(OBn)-CONH(CH$_2$)$_3$(2 -MeOPh) for (4-EtOPh)NHCO-D-His(Tr)-Tyr(OBn)-CONH(CH$_2$)$_3$OPh, the title compound was obtained as a white foam; ES-MS 674 (m+1).

EXAMPLE 27

(S,R)-N-[2-(4-Benzyloxy-phenyl)-1-phenethylcarbamoyl-ethyl]-3-(3H-imidazol-4-yl)-2-3-(4-phenoxy-phenyl)-ureido]-propionamide{(4-PhOPh)NHCO-D-His-Tyr(OBn)-CONH(CH$_2$)$_2$ Ph}

Step 1. Boc-Tyr(OBn)CONH(CH$_2$)2Ph

According to Example 25, Step 1, by substituting phenethylamine for 2-(phenylmethoxy)ethylamine, the title compound was obtained as a white solid; CI-MS 475 (m+1).

Step 2. Tyr(OBn)-CONH(CH$_2$)$_2$Ph

According to Example 25, Step 2, by substituting BocTyr (OBn)-CONH(CH$_2$)$_2$Ph for BocTyr(OBn)-CONH(CH$_2$)$_3$OPh, the title compound was obtained as a white solid; CI-MS 375 (m+1).

Step 3. Fmoc-D-His(Tr)-Tyr(OBn)-CONH(CH$_2$)$_2$Ph

According to Example 25, Step 3, by substituting Tyr(OBn)-CONH(CH$_2$)$_2$Ph for Tyr(OBn)-CONH(CH$_2$)$_3$OPh, the title compound was obtained as a foam; ES-MS 977 (m+1).

Step 4. Fmoc-D-His-Tyr(OBn)-CONH(CH$_2$)$_2$Ph

Fmoc-D-His(Tr)-Tyr(OBn)-CONH(CH$_2$)$_2$Ph (1.2 g, 1.6 mmol) in MeOH (5mL) was treated with Pyridine.HCl (catalytic). The resulting mixture was stirred at 65° C. overnight and concentrated in vacuo to obtain an oil which was purified by flash chromatography (SiO$_2$, CHCl$_3$:MeOH eluent) to give a white solid; ES-MS 734 (m+1)

Step 5. (4-PhOPh)NHCO-D-His-Tyr(OBn)-CONH(CH$_2$)$_2$Ph

Fmoc-D-His-Tyr(OBn)-CONH(CH$_2$)$_2$Ph (0.6 g, 0.8 mmol) in CH$_2$Cl$_2$ (5 mL) was treated with piperdine (0.14 g, 1.6 mmol). The resulting mixture was stirred 2 hours before concentrating in vacuo and purifying the resulting by flash chromatography (SiO$_2$, CHCl$_3$:MeOH eluent) to give D-His-Tyr(OBn)-CONH(CH$_2$)$_2$Ph. The foam was dissolved in CH$_2$C$_2$ (5 mL) and treated with 4-phenoxyphenyl isocyanate (0.05 g, 0.23 mmol). The resulting mixture was stirred 1 hour at room temperature, concentrated in vacuo, and purified the resulting oil by flash chromatography (SiO$_2$, CHCl$_3$:MeOH eluent) to obtain (4-PhOPh)NHCO-D-His-Tyr(OBn)-CONH(CH$_2$)$_2$Ph as a foam; ES-MS 723 (m+1).

EXAMPLE 28

(S,R)-N-[1-(4-Benzyloxy-benzyl)-2-(4-benzyl-piperazin-1-yl)-2-oxo-ethyl]-3-(3H-imidazol-4-yl)-2-(toluene-4-sulfonylamino)-propionamide{(4-MePh)SO$_2$-D-His-Tyr(OBn)-CO(4-Bn-piperazin-1-yl).HCl}

Step 1. Boc-Tyr(OBn)-CO(4-Bn-piperazin-1-yl)

According to Example 25, Step 1, by substituting 1-benzylpiperizine for 2-(phenylmethoxy)ethylamine, the title compound was obtained as a white solid; CI-MS 530 (m+1).

Step 2. Tyr(OBn)-CO(4-Bn-piperazin-1-yl)

According to Example 25, Step 2, by substituting Boc-Tyr(OBn)-CO(4-Bn-piperazin-1-yl) for Boc-Tyr(OBn)-CONH(CH$_2$)$_3$OPh, the title compound was obtained as a white solid; CI-MS 430 (m+1).

Step 3. Fmoc-D-His(Tr)-Tyr(OBn)-CO(4-Bn-piperazin-1-yl)

According to Example 25, Step 3, by substituting Tyr(OBn)-CO(4-Bn-piperazin-1-yl) for Tyr(OBn)-CONH(CH$_2$)$_3$OPh, the title compound was obtained as a foam; ES-MS 1032 (m+1).

Step 4. (4-MePh)SO$_2$-D-His(Tr)-Tyr(OBn)-CO(4-Bn-piperazin-1-yl)

Fmoc-D-His-Tyr(OBn)-CONH(CH$_2$)$_3$OPh, (0.7 g, 0.69 mmol) in CH$_2$Cl$_2$ (5 mL) was treated with piperidine (0.14 g, 1.6 mmol). The resulting mixture was stirred 2 hours before concentrating in vacuo and purifying the resulting oil by flash chromatography (SiO$_2$, CHCl$_3$:MeOH eluent) to give D-His-Tyr(OBn)-CONH(CH$_2$)$_2$Ph. The foam was dissolved in CH$_2$Cl$_2$ (5 mL) and treated with pyridine (0.05 g, 0.63 mmol) followed by 4-toluenesulfonyl chloride (0.12 g, 0.63 mmol). The resulting mixture was stirred 3 hours at room temperature, concentrated in vacuo, and purified the resulting oil by flash chromatography (SiO$_2$, CHCl$_3$:MeOH eluent) to obtain (4-MePh)SO$_2$-D-His(Tr)-Tyr(OBn)-CO(4-Bn-piperazin-1-yl); ES-MS 963 (m).

Step 5. (4-MePh)SO$_2$-D-His(Tr)-Tyr(OBn)-CO(4-Bn-piperazin-1-yl).HCl (4-MePh)SO$_2$-D-His(Tr)-Tyr(OBn)-CO(4-Bn-piperazin-1-yl) (0.21 g, 0.22 mmol) was treated with 80% aqueous HCl (3 mL) and heated to 80° C. for 5 minutes. The mixture was cooled and diluted with water (5 mL). The solid was filtered off, and the supernate was concentrated in vacuo to provide an oil. The oil was dissolved in water (15 mL), frozen, and lyophilized to provide (4-MePh)SO$_2$-D-His-Tyr(OBn)-CO(4-Bn-piperazin-1-yl).HCl; ES-MS 720 (m).

EXAMPLE 29

N$_\alpha$-[N-[(Phenylmethoxy)carbonyl]-L-histidyl]-O-(phenylmethyl)-N-methyl-N-[2-(phenylmethoxy)ethyl]-L-tyrosinamide{Cbz-His-Tyr(OBn)-CON(Me)CH$_2$CH$_2$OBn}

According to Example 19, Step 3, by substituting N-methyl-N-[2-(phenylmethoxy)ethyl]amine for 2-(phenylmethoxy)ethylamine, the title compound was prepared; FAB-MS 690 (m+1).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A compound of the Formula I:

wherein:

n=1 or 2;

A=CONHR$^3$, wherein R$^3$ is alkyl, (CH$_2$)$_m$-cycloalkyl, (CH$_2$)$_m$-aryl, (CH$_2$)$_m$-heteroaryl, or (CH$_2$)$_m$O-alkyl, and m=0, 1, 2, or 3;

R=independently H or Me;

Y=independently H or Me;

Z=independently H or Me;

R$^1$=H, CO-aryl, (CH$_2$)$_m$-aryl, O(CH$_2$)$_m$-cycloalkyl, O(CH$_2$)$_m$-aryl, or O(CH$_2$)$_m$-heteroaryl wherein m is as defined above and R$^1$ is located at either the meta or para position;

X=one to four substituents, including H, alkyl, CF$_3$, F, Cl, Br, I, HO, MeO, NO$_2$, NH$_2$, N(Me)$_2$, OP$_3$H$_2$, or CH$_2$PO$_3$H$_2$; and R$^2$= NR(CH$_2$)$_2$OR$^4$ wherein R is as defined above, R⁴=H or R³, provided that at least one of Y and Z is Me; an optical isomer, diastereomer, or a pharmaceutically acceptable salt thereof.

2. A compound according to claim 1 which is a compound of Formula II:

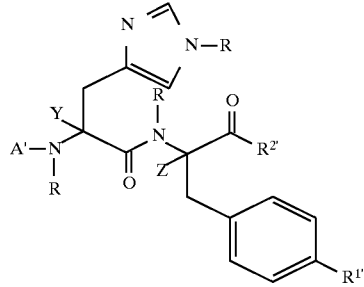

wherein:
A'=CONHR³, wherein R³ is alkyl, $(CH_2)_m$-cycloalkyl, $(CH_2)_m$-aryl, $(CH_2)_m$-heteroaryl, and m=0, 1, 2 or 3;
R=independently H or Me;
Y=independently H or Me;
Z=independently H or Me;
R¹'=$(CH_2)_m$-aryl, $O(CH_2)_m$-aryl, $OPO_3H_2$, or $CH_2PO_3H_2$, wherein m is as defined above;
R²'=$NR(CH_2)_2OR^4$ wherein R is as defined above,
R⁴=H or R³ provided that at least one of Y and Z is Me; an optical isomer, diastereomer, or a pharmaceutically acceptable salt thereof.

3. A compound selected from the group consisting of:
Cbz-His-Tyr(OBn)-D-Ser(OBn)-CO₂Me;
Cbz-D-His-Tyr(OBn)-Ser(OBn)-CONH₂;
Cbz-D-His-Tyr(OBn)-Ser(OBn)-CONHEt;
Cbz-D-His-Tyr(OBn)-Ser(OBn)-CO₂Me; and
Cbz-D-His-Tyr(OBn)-Ser(OBn).

4. A compound selected from the group consisting of:
Cbz-His(1-Me)-Tyr(OBn)-Ser(OBn)-CO₂Me;
Cbz-His(1-Me)-Tyr(OBn)-Ser(OBn)-CONH₂;
Cbz-His(1-Me)-Tyr(OBn)-Ser(OBn)-CONHEt;
Cbz-His(1-Me)-Tyr(OBn)-Ser(OBn);
Cbz-D-His(1-Me)-Tyr(OBn)-Ser(OBn)-CO₂Me;
Cbz-D-His(1-Me)-Tyr(OBn)-Ser(OBn)-CONH₂;
Cbz-D-His(1-Me)-Tyr(OBn)-Ser(OBn)-CONHEt; and
Cbz-D-His(1-Me)-Tyr(OBn)-Ser(OBn).

5. A compound selected from the group consisting of:
Cbz-His-(α-Me)Tyr(OBn)-Ser(OBn)-CO₂Me;
Cbz-His-(α-Me)Tyr(OBn)-Ser(OBn)-CONH₂;
Cbz-His-(α-Me)Tyr(OBn)-Ser(OBn)-CONHEt;
Cbz-His-(α-Me)Tyr(OBn)-Ser(OBn);
Cbz-His-D-(α-Me)Tyr(OBn)-Ser(OBn)-CO₂Me;
Cbz-His-D-(α-Me)Tyr(OBn)-Ser(OBn)-CONH₂;
Cbz-His-D-(α-Me)Tyr(OBn)-Ser(OBn)-CONHEt; and
Cbz-His-D-(α-Me)Tyr(OBn)-Ser(OBn).

6. A compound selected from the group consisting of:
Cbz-D-His-homoTyr(OBn)-Ser(OBn)-CO₂Me;
Cbz-His-Phe(4-Ph)-Ser(OBn)-CO₂Me;
Cbz-D-His-Phe(4-Ph)-Ser(OBn)-CO₂Me;
Cbz-His-Tyr(OBn)-Pyr-CO₂Me; and
Cbz-D-His-Tyr(OBn)-Pyr-CO₂Me.

7. A compound selected from the group consisting of:
Cbz-His-Tyr(OBn)-CONHCH₂CH₂OBn;
Cbz-D-His-Tyr(OBn)-CONHCH₂CH₂OBn;
Cbz-His-(N-Me)Tyr(OBn)-CONHCH₂CH₂OBn;
Cbz-D-His-(N-Me)Tyr(OBn)-CONHCH₂CH₂OBn;
Cbz-His-Tyr(OBn)-CONH(CH₂)₂Ph; and
Cbz-D-His-Tyr(OBn)-CONH(CH₂)₂Ph.

8. A compound selected from the group consisting of:
Cbz-His-Tyr(OBn)-Gly-CO₂Bn;
Cbz-D-His-Tyr(OBn)-Gly-CO₂Bn;
Cbz-His-Tyr(OBn)-Gly-CONHBn; and
Cbz-D-His-Tyr(OBn)-Gly-CONHBn.

9. A compound selected from the group consisting of:
BnNHCO-D-His-Tyr(OBn)-Ser(OBn)-CO₂Me;
BnNHCO-D-His-Tyr(OBn)-Ser(OBn)-CONH₂;
BnNHCO-D-His-Tyr(OBn)-Ser(OBn)-CONHEt;
BnNHCO-D-His-Tyr(OBn)-Ser(OBn);
BnNHCO-D-His-Tyr(OBn)-CONHCH₂CH₂OBn; and
BnNHCO-D-His-Tyr(OBn)-CONHCH₂CH₂CH₂OPh.

10. A compound selected from the group consisting of:
Cbz-His-Tyr(OBn)-CON(Me)CH₂CH₂OBn;
(4-EtOPh)NHCO-D-His-Tyr(OBn)-CONH(CH₂)₃OPh;
PhCH₂CO-D-His-Tyr(OBn)-CONH(CH₂)₃-(2-MeOPh)
(4-PhOPh)NHCO-D-His-Tyr(OBn)-COHN(CH₂)₂Ph; and
(4-MePh)SO₂-D-His-Tyr (OBn)-CO(4-Bn-piperazin-1-yl).

11. A pharmaceutical composition adapted for administration as an anticancer agent comprising a therapeutically effective amount of a compound according to claims 1, 2, 3, 4, 5, 6, 7, 8, 9, or 10 in admixture with a pharmaceutically acceptable excipient, diluent or carrier.

12. A pharmaceutical composition adapted for administration as a restenosis inhibiting agent comprising a therapeutically effective amount of a compound according to claims 1, 2, 3, 4, 5, 6, 7, 8, 9, or 10 in admixture with a pharmaceutically acceptable excipient, diluent, or carrier.

13. A method of treating ras-dependent cancer comprising administering to a host suffering therefrom a therapeutically effective amount of a compound having the Formula I:

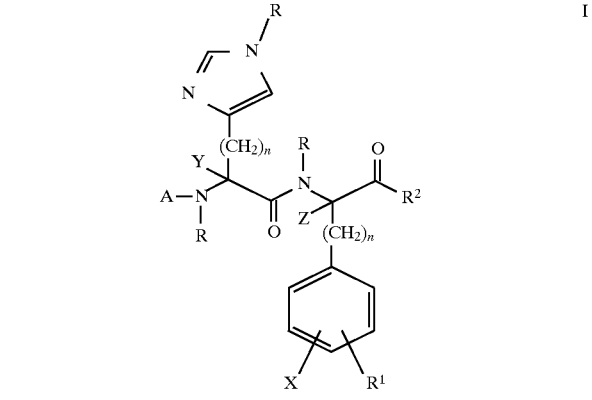

wherein:
n=1 or 2;
A=COR³, CO₂R³, CONHR³, CSR³, C(S)OR³, C(S)NHR³, CF₃SO₂, aryl-SO₂, or alkyl-SO₂, wherein R³ is alkyl, $(CH_2)_m$-cycloalkyl, $(CH_2)_m$-aryl, $(CH_2)_m$-heteroaryl, or $(CH_2)_m$O-alkyl, and m=0, 1, 2, or 3;
R=independently H or Me;
Y=independently H or Me;
Z=independently H or Me;
R¹=H, CO-aryl, $(CH_2)_m$-aryl, $O(CH_2)_m$-cycloalkyl, $O(CH_2)_m$-aryl, or $O(CH_2)_m$-heteroaryl wherein m is as defined above and R¹ is located at either the meta or para position;
X=one to four substituents, including H, alkyl, CF₃, F, Cl, Br, I, HO, MeO, NO₂, NH₂, N(Me)₂, OPO₃H₂, or CH₂PO₃H₂; and
R²=$NR(CH_2)_nCO_2R^3$, $NR(CH_2)_nCONHR^3$, $NR(CH_2)_nR^3$, $NR(CH_2)_{n+1}OR^4$ $NR(CH_2)_{n+1}SR^4$, $NRCH(COR^5)$ $(CH_2)_n$-heteroaryl, $NRCH(COR^5)$ $(CH_2)_nOR^3$, NRCH $(COR^5)$ $(CH_2)_n SR^3$,

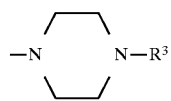

wherein R, $R^3$, and n are
as defined above, $R^4$=H or $R^3$, and $R^5$=OH, $NH_2$, $OR^3$, or $NHR^3$; an optical isomer, diastereomer, or a pharmaceutically acceptable salt thereof.

14. A method of treating restenosis comprising administering to a host suffering therefrom a therapeutically effective amount of a compound having the Formula I:

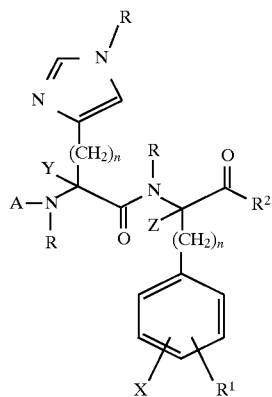

wherein:
n=1 or 2;

A=$COR^3$, $CO_2R^3$, $CONHR^3$, $CSR^3$, $C(S)OR^3$, $C(S)NHR^3$, $CF_3SO_2$, aryl-$SO_2$, or alkyl-$SO_2$, wherein $R^3$ is alkyl, $(CH_2)_m$-cycloalkyl, $(CH_2)_m$-aryl, $(CH_2)_m$-heteroaryl, or $(CH_2)_m$O-alkyl, and m=0, 1, 2, or 3;

R=independently H or Me;

Y=independently H or Me;

Z=independently H or Me;

$R^1$=H, CO-aryl, $(CH_2)_m$-aryl, $O(CH_2)_m$-cycloalkyl, $O(CH_2)_m$-aryl, or $O(CH_2)_m$-heteroaryl wherein m is as defined above and $R^1$ is located at either the meta or para position;

X=one to four substituents, including H, alkyl, $CF_3$, F, Cl, Br, I, HO, MeO, $NO_2$, $NH_2$, $N(Me)_2$, $OPO_3H_2$, or $CH_2PO_3H_2$; and $R^2$=$NR(CH_2)_nCO_2R^3$, $NR(CH_2)_nCONHR^3$, $NR(CH_2)_nR^3$, $NR(CH_2)_{n+1}OR^4$, $NR(CH_2)_{n+1}SR^4$, $NRCH(COR^5)(CH_2)_n$-heteroaryl, $NRCH(COR^5)(CH_2)_nOR^3$, $NRCH(COR^5)(CH_2)_nSR^3$,

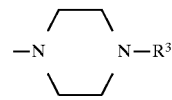

wherein R, $R^3$, and n are
as defined above, $R^4$=H or $R^3$, and $R^5$=OH, $NH_2$, $OR^3$, or $NHR^3$; an optical isomer, diastereomer, or a pharmaceutically acceptable salt thereof.

* * * * *